(12) United States Patent
Nishimura et al.

(10) Patent No.: US 9,182,390 B2
(45) Date of Patent: Nov. 10, 2015

(54) BIOMOLECULE-IMMOBILIZED CARRIER AND METHOD FOR IMMOBILIZING BIOMOLECULE ON CARRIER

(75) Inventors: Shin-Ichiro Nishimura, Sapporo (JP); Kentaro Naruchi, Sapporo (JP)

(73) Assignee: NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 721 days.

(21) Appl. No.: 12/735,837

(22) PCT Filed: Feb. 20, 2009

(86) PCT No.: PCT/JP2009/053038
§ 371 (c)(1),
(2), (4) Date: Nov. 29, 2010

(87) PCT Pub. No.: WO2009/104738
PCT Pub. Date: Aug. 27, 2009

(65) Prior Publication Data
US 2011/0091956 A1    Apr. 21, 2011

(30) Foreign Application Priority Data

Feb. 21, 2008 (JP) ................................ 2008-039890

(51) Int. Cl.
*G01N 33/543* (2006.01)
*C07K 17/14* (2006.01)
(Continued)

(52) U.S. Cl.
CPC ........ *G01N 33/54326* (2013.01); *C07K 14/205* (2013.01); *C07K 17/14* (2013.01);
(Continued)

(58) Field of Classification Search
None
See application file for complete search history.

(56) References Cited

U.S. PATENT DOCUMENTS

| 5,405,766 A | 4/1995 | Kallury et al. |
| 2003/0170826 A1 | 9/2003 | Rabinovich et al. |

FOREIGN PATENT DOCUMENTS

| JP | 2006-075103 A | 1/1990 |
| JP | H02-2938 A | 1/1990 |

(Continued)

OTHER PUBLICATIONS

Biochemistry.org "Lipids", Biochemistry, <URL: www.bioinfo.org.cn/book/biochemistry/chapt09/sim2.htm> , 2013 (accessed online Dec. 10, 2014), Chapter 9, 10 pages.*

(Continued)

*Primary Examiner* — Rosanne Kosson
*Assistant Examiner* — Aaron J Kosar
(74) *Attorney, Agent, or Firm* — DLA Piper LLP (US)

(57) ABSTRACT

Provided are a biomolecule-immobilized carrier obtained by immobilizing a biomolecule having a membrane-binding peptide containing a C terminal polypeptide of fucosyltransferase derived from *Helicobacter pylori* or a membrane-binding molecule having the membrane-binding peptide and various biomolecules and a method for immobilizing a biomolecule to a carrier, particularly a biomolecule-immobilized magnetic microparticle, a probe-immobilized carrier using the biomolecule and/or the membrane-binding molecule are/is used as a probe, and a separating agent for a biomolecule to which the biomolecule-immobilized magnetic microparticle is applied. A biomolecule having a membrane-binding peptide containing either an amino acid sequence represented by SEQ ID NO: 1 or an amino acid sequence encoded by a base sequence represented by SEQ ID NO: 2 and/or a membrane-binding molecule having the membrane-binding peptide and the biomolecule are/is attached to a carrier coated with an organic membrane containing a phospholipid.

11 Claims, 28 Drawing Sheets

(51) Int. Cl.

| | |
|---|---|
| *C07K 14/205* | (2006.01) |
| *C12N 9/10* | (2006.01) |
| *C12N 11/06* | (2006.01) |
| *C12N 9/24* | (2006.01) |

(52) U.S. Cl.
CPC ........... *C12N 9/1048* (2013.01); *C12N 9/1051* (2013.01); *C12N 9/2402* (2013.01); *C12N 11/06* (2013.01); *C12Y 204/01065* (2013.01); *C12Y 302/01018* (2013.01); *C07K 2319/03* (2013.01); *G01N 2333/91097* (2013.01)

(56) References Cited

FOREIGN PATENT DOCUMENTS

| JP | H10-075780 A | 3/1998 |
|---|---|---|
| JP | H11-106391 A | 4/1999 |
| JP | H11-243951 A | 9/1999 |
| JP | 2005-289822 A | 10/2005 |

OTHER PUBLICATIONS

"C-terminal amino acids . . . " written by Ma, B., et al. in Journal of Biological Chemistry, 2003, vol. 278, No. 24, pp. 21893-21900.

"Kinetic mechanism of *Staphylococcus aureus* sortase Srt A" written by Huang, X., et al. in Biochemistry, 2003, vol. 42, No. 38, pp. 11307-11315.

"Sortase-catalysed anchoring of surface proteins . . . " written by Mazmanian, S.K., et al., In Mol. Microbiol., 2001, vol. 40, No. 5, pp. 1049-1057.

"Cloning and heterologous expression of an α 1,3-fucosyltransferase . . . " written by GE. Z ., et al., in Journal of Biological Chemistry, 1997, vol. 272, No. 34, pp. 21357-212363.

"Structure and mechanism of *Helicobacter pylori* fucosyltransferase . . . " written by Sun, H-Y., et al., in Journal of Biological Chemistry, 2007, vol. 282, No. 13, pp. 9973-9982.

"Carboxyl terminus of *Helicobacter pylori* α1, 3-fucosyltransferase . . . " written by Lin, S-W., at al., in Biochemistry, 2006, vol. 45, No. 26, pp. 8108-8116.

"Crystal structures of *Staphylococcus aureus* sortase A and . . . " written by Zong,Y., et al., in Journal of Biological Chemistry, 2004, vol. 279, No. 30, pp. 31383-3138.

"Cell attachment activity of fibronectin can be duplicated by . . . " written by Pierschbacher, M. et al. in Nature, 1984, vol. 309, pp. 30-33.

"Creation of basement membrane" written by Mayumi Mochizuki, et al. in Protein Nucleic Acid and Enzyme, 2005, vol. 50, pp. 374-382.

"Incorporation of integrins into . . . " written by Eva-Kathrin Sinner et al. in Analytical Biochemistry of Academic Press Inc., Oct. 15, 2004, vol. 333, No. 2, pp. 216-224.

"The peptide-tethered lipid membrane as a biomimetic system to . . . " written by R. Naumann et al. in Biosensors & Bioelectronics, vol. 14, Oct. 1, 1999, pp. 651-662.

"Incorporation of the acetylcholine receptor dimmer from . . . " written by E.K. Schmidt et. al., in Biosensors & Bioelectronics, vol. 13, No. 6, Sep. 1, 1998, pp. 585-591.

"Membrane-Bound Stable Glycosyltransferases . . . " written by Kentaro Naruchi et al., in Angewandte Chemie International Edition, vol. 50, No. 6, Feb. 7, 2011, pp. 1328-1331.

Official Action of European Patent Application No. 09 711 582.8 issued by European Patent Office on Jan. 15, 2013, Sheets 1-2 & pp. 1-9.

Japanese language office action dated Sep. 24, 2013 and its partial English language translation issued in corresponding Japanese application 2009554396 , 8 pages.

Weber, Dominique A., et al "Transmembrane Domain-Mediated Colocalization of HLA-DM and HLA-DR is Required for Optimal HLA-DM Catalytic Activity" J. Immunol., Nov. 1, 2001, 167 (9), pp. 5167-5174. (doi: 10.4049/jimmunol.167.9.5167).

\* cited by examiner

BIOMOLECULE-IMMOBILIZED CARRIER AND METHOD FOR IMMOBILIZING BIOMOLECULE ON CARRIER

TECHNICAL FIELD

The present invention relates to a biomolecule-immobilized carrier and a method for immobilizing a biomolecule to carrier, particularly to a biomolecule- and/or membrane-binding molecule-immobilized magnetic microparticle, a probe-immobilized carrier using said biomolecule and/or said membrane-binding molecule as a probe and a separating agent for a biomolecule.

BACKGROUND ART

Since a magnetic microparticle can be magnetically collected, conventional researches focus on a technology for immobilizing a biomolecule, such as enzyme and antibody, to the magnetic microparticle. For example, Japanese Unexamined Patent Application Publications No. 1998-075780 and 1999-243951 disclose a magnetic microparticle to which an enzyme is directly immobilized by a conventional chemical method (Patent Documents 1 and 2). Meanwhile, Japanese Unexamined Patent Application Publication No. 2005-289822 discloses a membrane-fusion magnetic microparticle (magnetosome) derived from a magnetic bacterium to which a peptide is anchored (Patent Document 3), and Japanese Unexamined Patent Application Publication No. 2006-075103 discloses a membrane-fusion magnetosome derived from a magnetic bacterium obtained by expressing a fusion protein composed of an anchor protein MMs13 and an IgG-binding peptide in vivo (Patent Document 4).

Meanwhile, some polypeptides having cellular adhesiveness are conventionally known, e.g. syndecan-binding laminin-derived polypeptide as extracellular sugar chain (Non-Patent Document 1), Arg-Gly-Asp (RGD) tripeptide sequence derived from fibronectin (Non-Patent Document 2) as integrin ligand sequence, or a polypeptide present on a C terminal side of α1,3-fucosyltransferase and α1,4-fucosyltransferase derived from *Helicobacter pylori* (Non-Patent Document 3 and 4) as polypeptide having cell membrane adhesiveness. It is also known that the polypeptide present on a C terminal side of α1,3/α1,4-fucosyltransferase derived from *Helicobacter pylori* is provided with an α-helix structure, thereby providing a property of binding to a cell membrane (Non-Patent Document 3).

Patent Document 1: Japanese Unexamined Patent Application Publication No. 1998-075780
Patent Document 2: Japanese Unexamined Patent Application Publication No. 1999-243951
Patent Document 3: Japanese Unexamined Patent Application Publication No. 2005-289822
Patent Document 4: Japanese Unexamined Patent Application Publication No. 2006-075103
Non-Patent Document 1: Pierschbacher, M. et al. Nature, 309, 303-303, 1984
Non-Patent Document 2: Mayumi Michizuki, Yuichi Kadoya, Motoyoshi Nomizu, Tanpakushitu kakusan koso (Protein nucleic acid enzyme), 50, 374-382, 2005
Non-Patent Document 3: J. Biol. Chem., 278, 21893-21900, 2003
Non-Patent Document 4: J. Biol. Chem., 282, 9973-9982, 2007

DISCLOSURE OF THE INVENTION

Problem to be Solved by the Invention

However, a magnetic microparticle disclosed in Patent Documents 1 and 2 is not given any specific properties on a repeated use thereof, other than a possible enzyme deactivation in an immobilizing reaction due to use of a chemical method, resulting in less reliable durability and biomolecule activity persistence. In addition, the magnetic microparticle causes a serious difficulty in controlling molecular orientation.

A magnetic microparticle disclosed in Patent Documents 3 and 4 is an extremely hydrophobic transmembrane peptide used as an anchor protein. Furthermore, Patent Document 3 discloses no successful technologies for utilizing a magnetic microparticle from a biomolecule such as enzyme as a useful protein anchored onto the magnetic microparticle, and Patent Document 4 discloses problems of encapsulation and flocculation due to expression of transmembrane peptide and target protein as a fusion protein. To solve these problems, it is necessary to prevent flocculation by treating a magnetic microparticle for solubilization using a surfactant of high concentration, but resultant deactivation of an enzyme, etc. by the surfactant can make a use of the magnetic microparticle difficult with an activity of the enzyme, etc. maintained.

To solve these problems, it is, therefore, one object of the present invention to provide a biomolecule-immobilized carrier, comprising immobilizing a biomolecule having a membrane-binding peptide containing a C terminal polypeptide of fucosyltransferase derived from *Helicobacter pylori* or a membrane-binding molecule having the membrane-binding peptide and various biomolecules and a method for immobilizing a biomolecule to a carrier, particularly a biomolecule-immobilized magnetic microparticle, a probe-immobilized carrier using the biomolecule and/or the membrane-binding molecule used as a probe, and a separating agent for a biomolecule to which the biomolecule-immobilized magnetic microparticle is applied.

Means for Solving the Problem

The inventors successfully completed this invention by finding out a property of the above-mentioned known C terminal polypeptide of α1,3/α1,4-fucosyltransferase derived from *Helicobacter pylori* to firmly bind to an organic membrane containing a phospholipid (e.g. biomembrane and biomimetic membrane) as well and an ability of an α-helix structure to control molecular orientation according to a property of the C terminal polypeptide of α1,3/α1,4-fucosyltransferase derived from *Helicobacter pylori* to firmly bind to a cell membrane, a property to be solubilized in an aqueous solvent due to high charge and a property to have an α-helix structure when binding to a cell membrane.

Specifically, the present invention comprises the following items:

[1] A biomolecule-immobilized carrier, comprising binding a biomolecule having a membrane-binding peptide containing either an amino acid sequence represented by SEQ ID NO: 1 or an amino acid sequence encoded by a base sequence represented by SEQ ID NO: 2 and/or a membrane-binding molecule having said membrane-binding peptide and the biomolecule to a carrier coated with an organic membrane containing a phospholipid;

[2] The biomolecule-immobilized carrier according to item [1], wherein said carrier is a magnetic microparticle, or a probe-immobilized carrier using a biomolecule having said membrane-binding peptide and/or said membrane-binding molecule as a probe;

[3] The biomolecule-immobilized carrier according to item [1] or [2], wherein said biomolecule is an enzyme or a sugar chain;

[4] The biomolecule-immobilized carrier according to item [3], wherein said enzyme is glycosyl transferase or glycosidase;

[5] A separating agent for a biomolecule, comprising binding a biomolecule having a membrane-binding peptide containing either an amino acid sequence represented by SEQ ID NO: 1 or an amino acid sequence encoded by a base sequence represented by SEQ ID NO: 2 and/or a membrane-binding molecule having said membrane-binding peptide and the biomolecule to a magnetic microparticle coated with an organic membrane containing a phospholipid; and

[6] A method for immobilizing a biomolecule to a carrier which is a method for directly or indirectly immobilizing a biomolecule to a carrier with bioactivity maintained, comprising a phospholipid modifying step for modifying a fixed ligand to be immobilized to the carrier to a phospholipid, a carrier coating step for forming and coating an organic membrane on a surface of the carrier using a phospholipid which modifies said fixed ligand, and a binding step for binding a biomolecule having a membrane-binding peptide containing either an amino acid sequence represented by SEQ ID NO: 1 (Lys-Ile-Tyr-Arg-Lys-Ala-Tyr-Gln-Lys-Ser-Leu-Pro-Leu-Leu-Arg-Thr-Ile-Arg-Arg-Trp-Val-Lys-Lys) or an amino acid sequence encoded by a base sequence represented by SEQ ID NO: 2 (5'AAAATCTATCGCAAAGCCTA TCAAAAATCCTTACCTTTGTTGCGCAC-CATAAGGAGATGGGTTAAAAAA3') and/or a biomolecule to which said membrane-binding peptide is fused or bound as a linker to said organic membrane. In the embodiment represented in FIG. 18, amino acid sequence DRLLQ-NASPLLELSQNTTFKIYRKAYQKSLPLLRTIRRWVKK is SEQ ID NO: 8 and amino acid sequence LPETGDRLLQ-NASPLLELSQNTTFKIYRKAYQKSLPLLRTIRRWVKK is SEQ ID NO: 9.

Advantageous Effect of the Invention

The present invention can provide a biomolecule-immobilized carrier capable of controlling molecular orientation with biomolecule activity maintained due to excellent durability and being readily handled due to solubilization of a membrane-binding molecule, particularly a biomolecule-immobilized magnetic microparticle, a probe-immobilized carrier using a biomolecule having said membrane-binding peptide and/or said membrane-binding molecule as a probe, and a separating agent for a biomolecule to which the biomolecule-immobilized magnetic microparticle is applied, in addition to a method for immobilizing a biomolecule to a carrier.

BEST MODE FOR CARRYING OUT THE INVENTION

Figure 1:
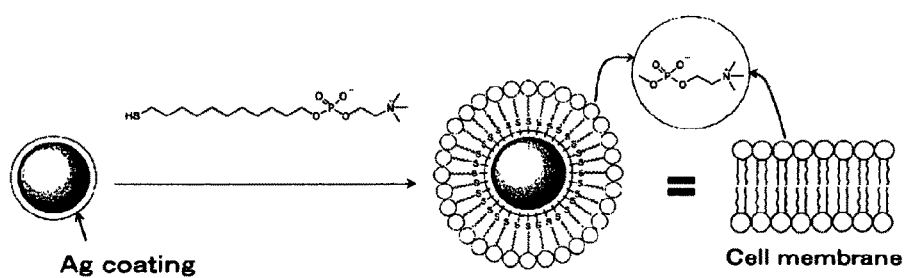
FIG. 1 is a diagram showing a process for preparing a biomembrane mimetic magnetic microparticle in Example 1(2).

A biomolecule-immobilized carrier and a method for immobilizing a biomolecule to a carrier according to the present invention will be described in detail.

A biomolecule-immobilized carrier according to the present invention comprises binding a biomolecule having a membrane-binding peptide containing either an amino acid sequence encoded by an amino acid sequence represented by SEQ ID NO: 1 or a base sequence represented by SEQ ID NO: 2 and/or a membrane-binding molecule having said membrane-binding peptide and the biomolecule to a carrier coated with an organic membrane containing a phospholipid.

The membrane-binding peptide containing either an amino acid sequence encoded by amino acid sequence represented by the SEQ ID NO: 1 or a base sequence represented by SEQ ID NO: 2 is provided with a property of reversibility, i.e. a random structure in an aqueous solvent to be solubilized, but an α-helix structure in neutrality and in the presence of a phospholipid. Specifically, the membrane-binding peptide, which is, under neutrality conditions, of an α-helix structure to bind to an organic membrane, will be of a random structure under alkaline conditions (pH as approximately 10) to desorb from the organic membrane. According to the inventors, etc., it is also known that the membrane-binding peptide cannot be provided with an α-helix structure again only by lowering pH to make the membrane-binding peptide neutral, but it can be provided with an α-helix structure again in the presence of a phospholipid.

Conformational analysis of a membrane-binding peptide is not particularly limited in method, but in an embodiment according to the present invention, conformational analysis is performed by a method for measuring circular dichroism (CD).

"Bind(ing)" in this invention generally means that A is bound to B, or A binds to B, and two objects make contacts on the surface and the state is kept. In this invention, this term is interchangeably used as "immobilize (immobilizing)" or "immobilization." Specifically, it means that other than a case in which a membrane-binding portion of a membrane-binding peptide and a surface of an organic membrane make contacts, a membrane-binding portion of a membrane-binding peptide and an organic membrane in this invention remain touched in such a way that the membrane-binding portion gets into or through the organic membrane.

"Having a membrane-binding peptide" in this invention means not only integration of a membrane-binding peptide into a membrane-binding portion having a membrane-binding ability, but also complete conversion of a membrane-binding peptide to a membrane-binding portion. In addition, except for a case in which a biomolecule naturally has a membrane-binding peptide such as fucosyltransferase derived from *Helicobacter pylori*, a biomolecule might have a membrane-binding peptide by making a biomolecule fuse or bind to a membrane-binding peptide, as shown in a membrane-binding molecule comprising fusing or binding a membrane-binding peptide to e.g. maltose-linked protein-fused galactose transferase (MBP-GalT), O-linked glycopeptide or N-acetylgalactosamine transferase 2 (ppGalNAcT2).

A biomolecule in this invention is a molecule which naturally has a membrane-binding peptide or a molecule which can fuse or bind to a membrane-binding peptide, and it is not particularly limited as long as the molecule is synthesized, metabolized and stored in vivo, e.g. DNA, RNA, PNA, aptamer, gene, chromosome, peptide, enzyme, receptor, sugar compound (monosaccharide, oligosaccharide, polysaccharide, sugar chain complex, glycoprotein, glycolipid, their derivative, etc), lipid (fatty acid, phospholipid, glycolipid, glyceride, etc), antibody, antigen, hapten, hormone, virus, natural low-molecule (hormone molecule, antibiotic, toxic substance, vitamins, bioactive substance, secondary metabolite, etc), and synthetic low molecule (synthetic substance of natural low molecule, their derivative, etc). In an embodiment according to the present invention, an enzyme and a sugar chain are used as a favorable biomolecule, and a glycosyl transferase and a glycosidase are used as a favorable enzyme.

A membrane-binding molecule in this invention includes a membrane-binding peptide and a biomolecule, particularly a molecule in which these two individual substances are fused or bound. This type of biomolecule might include a membrane-binding peptide as one substance.

A membrane-binding molecule in this invention may contain some or no other substances as long as a membrane-binding ability of a membrane-binding peptide and functions of a biomolecule are not impaired. In an embodiment according to the present invention, there might exist between a membrane-binding peptide and a biomolecule a repeated sequence composed of 7 residues (Asp-Asp-Leu-Arg-Val-Asn-Tyr) (SEQ ID NO: 5) called Heptad Repeat and a sequence composed of 5 residues (Leu-Pro-Glu-Thr-Gly) (SEQ ID NO: 6).

A membrane-binding molecule in this invention can be prepared by fusing or binding a membrane-binding peptide and a biomolecule, using genetic recombinant techniques, enzyme reaction, linker, etc. For example, in cases where the biomolecule is a protein, a membrane-binding peptide and a biomolecule can be fused and expressed as a membrane-binding molecule to prepare a membrane-binding molecule using genetic recombinant techniques, and a membrane-binding peptide and a protein can be fused or bound to prepare a membrane-binding molecule using an enzyme, etc. For example, sortase A (SrtA) enzyme, which binds a peptide having an amino acid sequence LPETG (Leu-Pro-Glu-Thr-Gly) (SEQ ID NO: 6) and a peptide having an amino acid sequence GGG (Gly-Gly-Gly; triglycine), can be used to prepare a membrane-binding molecule.

For example, in cases where a biomolecule is a sugar chain, a consensus sequence is linked to a sequence encoding a membrane-binding peptide to add a sugar chain thereto by genetic recombinant techniques to express genes in cells having a sugar chain-adding ability such as CHO cell, COS cell and yeast cell, thereby preparing a membrane-binding peptide as a glycopeptide. Also, a membrane-binding peptide can be prepared by fusing or binding a membrane-binding peptide and a sugar chain, using a favorable linker.

A biomolecule and a membrane-binding molecule in this invention are, under alkaline conditions, released from a carrier coated with an organic membrane containing a phospholipid, and can be immobilized again in neutrality and in the presence of an phospholipid. Even with a repeated use thereof, adhesiveness of a molecule of a membrane-binding peptide, enzyme activity and sugar chain function can be maintained.

In cases where a biomolecule and a membrane-binding molecule are obtained by purification, a purification method thereof is not particularly limited as long as it can be selected by those skilled in the art accordingly, and it can be any method such as each type of chromatography and mass spectrometry. Gel filtration column chromatography, reversed-phase high-performance liquid chromatography (RP-HPLC) and Matrix Assisted Laser Desorption/Ionization Time Of Flight Mass Spectrometer (MALDI-TOF-MS) are used in an embodiment according to the present invention.

A phospholipid in this invention is one having two or more hydrophobic groups composed of phosphate group and acyl group and/or alkyl group in a molecule, e.g. phosphatidyl choline (lecithin), phosphatidyl ethanolamine, phosphatidyl inositol, phosphatidyl inositol-4-phosphoric acid, phosphatidyl inositol 4,5-diphosphoric acid, phosphatidyl serine, phosphatidylglycerol, diphoshatidylglycerol, phosphatidic acid, sphingomyelin or a mixture containing one or two of these derivatives, etc. Phosphatidyl choline is used as a favorable phospholipid in an embodiment according to the present invention.

A fatty acid comprising a phospholipid in this invention is not particularly limited, but it can be a saturated or unsaturated fatty acid such as caprylic acid, lauric acid, myristic acid, palmitic acid, stearic acid, behenic acid, arachic acid, palmitoleic acid, oleic acid, linoleic acid, α- and γ-linoleic acid, erucic acid, arachidonic acid, eicosapentaenoic acid, docosahexaenoic acid and tetracosa tetraenoic acid.

Herein, "organic membrane containing a phospholipid" in this invention means, for example, not only an organic membrane formed by linking a fixed ligand to be immobilized to a carrier which is modified (bound) to a phospholipid to the carrier (biomimetic membrane), but also e.g. an organic membrane formed by forming and adsorbing a polymer containing a phospholipid (biomimetic membrane) and an organic membrane formed by directly linking a phospholipid to a carrier (biomimetic membrane). Specifically, this means a case in which a phospholipid is not only partially, but also completely comprises an organic membrane (biomimetic membrane).

In cases where said fixed ligand is modified to a phospholipid, the fixed ligand can be selected according to a phospholipid and a carrier, e.g. thiol group, epoxy group, tosyl group, activated ester, amino group and bromoacetamide, etc which can be modified (linked) to a terminus of acyl group and/or alkyl group of a phospholipid. When a polymer containing said phospholipid is used, it can be selected according to a carrier, e.g. methacrylate polymer in which phosphocholine group is dispersed. In an embodiment according to the present invention, phosphatidyl choline is used as a favorable phospholipid, and thiol group which can be modified (bound) to a terminus of alkyl group of phosphatidyl choline is used as a favorable fixed ligand, which is subsequently linked a carrier to form an organic membrane (biomimetic membrane).

A carrier in this invention can be selected according to a purpose of use as long as it can be coated with an organic membrane containing a phospholipid, e.g. organic polymer compound in which polymerizable monomers such as magnetic microparticle, styrenic polymerizable monomer, acrylic polymerizable monomer, methacrylic polymerizable monomer and vinyl polymerizable monomer are polymerized, metal oxide, metal, semiconductor compound, agarose, SEPHAROSE™, wooden plate, glass plate, silicon substrate, cotton cloth, rayon cloth, acrylic cloth, silk cloth, polyester cloth, wood-free paper, wood-containing paper, art paper, bond paper, recycled paper, baryta paper, cast-coated paper, corrugated paper and resin-coated paper. In an embodiment according to the present invention, magnetic microparticle, organic polymer compound (plastic substrate) and glass substrate are used as a favorable carrier.

In cases where a magnetic microparticle is used as a carrier in this invention, magnetic microparticle can be selected accordingly, e.g. metal or oxide, ferrite microparticle as a chemically stable ferric oxide, magnetite microparticle and maghemite microparticle. Also, the magnetic microparticle contains such elements as Ag, Li, Mg, Fe, Mn, Co, Ni, Cu, Y, Sm and Zn, and it may be selected according to a purpose of use. In an embodiment according to the present invention, Ag-coated magnetic microparticle as a ferrite microparticle is used as a favorable magnetic microparticle. Magnetic microparticle is not particularly limited in diameter, but it is preferably 10 nm to 500 nm.

A biomolecule-immobilized magnetic microparticle according to the present invention comprises a biomolecule having a membrane-binding peptide and/or a membrane-binding molecule having said membrane-binding peptide and the biomolecule, and a magnetic microparticle coated with an organic membrane containing a phospholipid. Specifically, the biomolecule and/or the membrane-binding molecule are immobilized to the organic membrane covering the magnetic microparticle, with adhesiveness of the membrane-binding peptide and biomolecule functions maintained. It is also possible to control orientation of the biomolecule and/or the membrane-binding molecule. Since biomolecule activity can be maintained and magnetically be collected, the biomolecule-immobilized magnetic microparticle can be used for various purposes. In an embodiment according to the present invention, it comprises a microarray and a separating agent for a biomolecule.

A probe-immobilized carrier using a biomolecule having a membrane-binding peptide and/or a membrane-binding molecule as a probe according to the present invention comprises a probe as a biomolecule and/or a membrane-binding molecule and a carrier coated with an organic membrane containing a phospholipid. Specifically, the probe-immobilized carrier is immobilized to an organic membrane with a biomolecule and/or a membrane-binding molecule covering the carrier, and the biomolecule and/or the membrane-binding molecule function as a probe.

A carrier of a probe-immobilized carrier using a biomolecule having a membrane-binding peptide and/or a membrane-binding molecule as a probe in this invention can be selected accordingly as long as the probe is immobilized to a carrier coated with an organic membrane containing a phospholipid and target substances can be successfully detected or separated using the probe-immobilized carrier, e.g. the aforementioned carrier, preferably solid carrier, and in case of microarray, glass substrate and plastic substrate are preferable in view of target substance detection and versatility, and alkali-free glass substrate and quartz substrate are more preferable. In an embodiment according to the present invention, 96-hole plate and glass slide-embedded MTP-Slide-AdaptorII (Bruker) are used.

An enzyme which is used as a biomolecule in this invention is not particularly limited, but e.g. oxidoreductase, transferase, hydrolase, lyase, isomerase and ligase. In this invention, it is preferably transferase or hydrolase, and more preferably glycosyl transferase or glycosidase. In this invention, any glycosyl transferase can be used, e.g. fucosyltransferase, galactose transferase, sialidase, N-acetylgalactosamine transferase, N-acetylglucosaminyl transferase, mannosyltransferase, β-glucuronyl transferase, β-xylosyltransferase and glucosyltransferase. In an embodiment according to the present invention, fucosyltransferase, maltose-linked protein-fused galactose transferase (MBP-GalT), N-acetylgalactosamine transferase2 (ppGalNAcT2) and sialidase are used.

A sugar chain in this invention is not particularly limited, but it may be a sugar chain composed of O-linked sugar chain or N-linked sugar chain, or a combination of O-linked and N-linked sugar chains. Herein, O-linked sugar chain is generically called as various types of sugar chain structures elongating from N-acetylgalactosamine linked to serine residues existing in a primary structure of a protein or threonine residues, e.g. a sugar chain in which GalNAc is bound to OH group of Ser or Thr through C—O binding. N-linked sugar chain is generically called as various types of sugar chain structures elongating from N-acetylgalactosamine linked to asparagine residues for a primary structure of a protein, e.g. a sugar chain containing GlcNAc linked to $NH_2$ group of Asn of Asn-X-(Ser/Thr) through C—N binding as a reducing terminal.

A method for immobilizing a biomolecule to a carrier according to the present invention is a method for directly or indirectly immobilizing a biomolecule fused or bound using a membrane-binding peptide as a linker, to an organic membrane containing a phospholipid, with bioactivity thereof maintained, specifically a method for immobilizing a biomolecule to an organic membrane by making contacts between a hydrophilic amino-acid side chain of a membrane-binding peptide and a hydrophilic group of the organic membrane, via the membrane-binding peptide (a biomolecule might have the peptide) and the organic membrane (biomimetic membrane). The inventors, etc. successfully completed a method for immobilizing a biomolecule to a carrier according to the present invention after long-term careful researches, by finding that said membrane-binding peptide is provided with an α-helix structure by which a hydrophilic amino-acid side chain is oriented in a prescribed direction, a hydrophilic group of said organic membrane coating the carrier is oriented in the direction of surface, and biomolecule orientation control can immobilize a biomolecule to an organic membrane (biomembrane, biomimetic membrane) by making the hydrophilic amino-acid side chain of the membrane-binding peptide and the hydrophilic group of the organic membrane bind.

By immobilizing a biomolecule to an organic membrane via a membrane-binding peptide (a biomolecule might have the peptide) and an organic membrane (biomimetic membrane), using a method for immobilizing a biomolecule to a carrier according to the present invention, it is possible to control biomolecule orientation and to immobilize the biomolecule to the organic membrane with bioactivity maintained, thereby providing an effect of maintaining biomolecule bioactivity even with a repeated use of resultant substances from immobilization. Since the organic membrane containing a phospholipid can be formed by being readily coated on any carrier, a membrane-binding molecule-immobilized carrier, containing a mixture composed of any biomolecule and any carrier, can be produced by a method for immobilizing a biomolecule to a carrier according to the present invention.

Meanwhile, a method for producing a membrane-binding molecule in vivo according to the present invention comprises the following processes (i) to (v):
(i) A process for amplifying DNA fragments by PCR method by designing a primer encoding an amino acid sequence represented by SEQ ID NO: 1;
(ii) A process for constructing a biomolecule-expressing vector which constructs a vector expressing a biomolecule;
(iii) A process for constructing a membrane-binding molecule-expressing vector which constructs a vector expressing a membrane-binding molecule from DNA fragments and a biomolecule-expressing vector;
(iv) A process for preparing an expressing cell line which prepares an expressing cell line by introducing a membrane-binding molecule-expressing vector; and (v) A process for collecting a membrane-binding molecule which collects a membrane-binding molecule by culturing an expressing cell line.

A process for amplifying DNA fragments in process (i) is a process for designing a primer encoding an amino acid sequence represented by SEQ ID NO: 1 according to a conventional method and amplifying DNA fragments by PCR method. A typical method is to identify an annealed portion of the primer, perform Blast search using a sequence of a target area, design a primer by homology analysis of a downloaded sequence and perform PCR by confirming a primer. In view of PCR efficiency and other factors, DNA fragments whose amplifying size ranges approximately 500 to 1000 bases are desirable.

A base sequence of target DNA fragments can be confirmed by known methods such as Dideoxynucleotide Chain Termination Method (Sambrook, J. et al., Molecular Cloning, Cold Spring Harbor Laboratory Press, 1989), and automatic base sequence-determining apparatus (for example, DNA Sequencer PRISM 377 or DNA Sequencer PRISM 310; both from Perkin-Elmer) can be used. Also, DNA fragment modification can be performed using commercially available kits and known methods, such as digestion by restriction enzyme, insertion of synthetic oligonucleotide and appropriate DNA fragments, addition of a linker and insertion of start codon (ATG) and/or termination codon (TAA, TGA, or TAG).

A process for constructing a biomolecule-expressing vector in process (ii) is a process for constructing a biomolecule-expressing vector according to a conventional method, such as a method described in Berg, P. et al., Proc. Nat. Acad. Sci. USA, 69, 2904-2909, 1972. Herein, a vector used in this invention can be selected by those skilled in the art accordingly, and it is not specifically limited, but it can be, e.g. pCOS1, pME18S, pEF-BOS, pCDM8, pRSVneo, pSV2-neo, pcDNAI/Amp, pcDNAI, pAMoERC3Sc, pAGE107, pREP4, pAGE103, pAMoA, pAS3-3, pCAGGS, pBK-CMV, pcDNA3.1 and pZeoSV.

In addition, a biomolecule-expressing vector can be constructed using a commonly used promoter, such as human polypeptide chain elongation factor 1α (HEF-1α). An expression vector containing HEF-1α promoter is, e.g. pEF-BOS (Mizushima, S. et al., Nuc. Acid. Res. 18, 5322, 1990). A gene promoter can be virus promoter such as cytomegalovirus, retrovirus, polyomavirus, adenovirus, simian virus 40 (SV40), and promoter derived from mammal cell.

Also, a biomolecule-expressing vector can contain a selectable marker gene, such as phosphotransferase APH (3') II or I (neo) gene, thymidine kinase gene, E. coli xanthine-guanine phosphoribosyltransferase (Ecogpt) gene and dihydrofolate reductase (DHFR) gene.

A process for constructing a membrane-binding molecule-expressing vector in process (iii) is a method for constructing a membrane-binding molecule-expressing vector by conventional methods, using DNA fragments amplified in process (i) and a biomolecule-expressing vector constructed in process (ii). For example, a membrane-binding molecule-expressing vector can be constructed as in process (ii).

A process for preparing an expressing cell line in process (iv) is a process for preparing an expressing cell line by introducing a membrane-binding molecule-expressing vector constructed in process (iii) to a cell by conventional methods. A cell to which a membrane-binding molecule-expressing vector is introduced can be selected by those skilled in the art accordingly, such as animal cell, E. coli and yeast, and it is not specifically limited, but preferably E. coli. A typical cell is JM109 or DH5α. In an embodiment according to the present invention, E. coli JM109 strain is used as a favorable cell.

A membrane-binding molecule-expressing vector is introduced by a known method, such as calcium phosphate method (Chen, C. et al., Mol. Cell. Biol., 7, 2745-2272, 1987), lipofection method (Feigner, P L. et al., Proc. Natl. Acad. Sci. USA, 84, 7413-7417, 1987) and electroporation method (Potter, H. Anal. Biochem., 174, 361-373, 1988). In the electroporation method, gene introduction apparatus (Gene Pulser; Bio-Rad) can be used.

A process for collecting a membrane-binding molecule in process (v) is a process for culturing an expressing cell line prepared in process (iv) by conventional methods and solubilizing and collecting a membrane-binding molecule expressed in an expressing cell line under alkaline conditions. The expressing cell line is crushed by a known method, but in an embodiment according to the present invention, it is preferably a method for crushing an expressing cell line, using an ultrasonic crusher.

Next, a method for producing a biomolecule-immobilized carrier according to the present invention comprises the following processes (i) to (iii):
(i) A process for forming a biomembrane-mimicking carrier which forms a biomembrane-mimicking carrier by coating a carrier with an organic membrane containing a phospholipid;
(ii) A process for preparing an immobilized biomolecule which prepares a biomolecule having a membrane-binding peptide and/or a membrane-binding molecule having said membrane-binding peptide and the biomolecule; and
(iii) A process for immobilizing a membrane-binding molecule to a biomembrane-mimicking carrier in neutrality and in the presence of a phospholipid, using a membrane-binding peptide as a linker.

A process for forming a biomembrane-mimicking carrier in process (i) is a process for forming a biomembrane-mimicking carrier by coating a magnetic microparticle and a carrier such as solid carrier with an organic membrane containing a phospholipid. Specifically, a hydrophobic group of a phospholipid is arrayed in the direction of a carrier by binding the hydrophobic group of a phospholipid to a surface of the carrier, resulting in arraying of the hydrophilic group of a phospholipid outwardly to coat a surface of the carrier on a biomembrane-like organic membrane. In this invention, a carrier whose surface is coated with a biomembrane-like organic membrane is defined as a biomembrane-mimicking carrier. A fixed ligand to be immobilized to a carrier may be modified to a phospholipid as required.

A process for preparing an immobilized biomolecule in process (ii) is a process for preparing a biomolecule having a membrane-binding peptide and/or a membrane-binding molecule having said membrane-binding peptide and the biomolecule in vitro or in vivo. As mentioned above, the process includes a case in which not only a fused molecule in which two individual substances of the membrane-binding peptide and the biomolecule are fused or bound is prepared, but also a biomolecule having the membrane-binding peptide as a substance is prepared.

A process for immobilizing a membrane-binding molecule to a biomembrane-mimicking carrier in process (iii) is a process for immobilizing a biomembrane-mimicking carrier formed by a process for forming a biomembrane-mimicking carrier in process (i) and a biomolecule and/or a membrane-binding molecule prepared by a process for preparing an immobilized biomolecule in process (ii) in neutrality via a membrane-binding peptide in the biomolecule and/or the membrane-binding molecule. Specifically, in a process for immobilizing a membrane-binding molecule to a biomembrane-mimicking carrier in process (iii), a method for immobilizing a biomolecule to a carrier for immobilizing a biomolecule is used with bioactivity maintained in an organic membrane containing a phospholipid according to the present invention.

A membrane-binding molecule-immobilized carrier and a method for immobilizing a biomolecule to a carrier according to the present invention will be described with reference to Examples. A technological scope in this invention is not limited to characteristics as shown in the Examples.

EXAMPLE

Example 1

Preparation of Fucosyltransferase-Immobilized Magnetic Microparticle and Measurement of Enzyme Activity α-1,3 fucosyltransferase derived from *Helicobacter pylori* includes said membrane-binding peptideon on a C terminal side. Then, the fucosyltransferase is presented to a biomembrane mimetic (organic membrane-coating) magnetic microparticle to measure enzyme activity of fucosyltransferase-immobilized magnetic microparticle obtained.

(1) Expression and Purification of Fucosyltransferase

α-1,3 fucosyltransferase derived from *Helicobacter pylori* J99B strain was expressed by recombinant *E. coli* to be purified. Specifically, after a recombinant *E. coli* expressing α-1,3 fucosyltransferase derived from *Helicobacter pylori* J99B strain (Taylor, D. E. et al., J. Biol. Chem., 278, 21893-21900, 2003) was cultured in 2 L of a YT medium obtained by diluting twice at 37° C. for 8 hours, isopropylthiogalactoside was added thereto so that a final concentration thereof reached 1 mM and cultured at 20° C. for 20 hours. A culture solution was subjected to centrifugal separation at 10,000×g for 20 minutes to collect bacterial cells. The collected bacterial cells were suspended in 5 mL of 25 mM Tris buffer solution (pH8.0) containing 1 mM mercaptoethanol and 10% (w/v) glycerol and were subjected to ultrasonic crushing by ultrasonic crusher under cooling five times for 2 minutes each. After another centrifugal separation at 10,000×g for 20 minutes, supernatants were collected to perform affinity purification by nickel column (His Trap FF; Amersham Pharmacia Biotech). After fractions containing fucosyltransferase were substituted by dialysis using 25 mM glycine-sodium hydroxide buffer solution (pH10) and subjected to an anion-exchange column (HiTrap Q HP; Amersham Pharmacia Biotech) under alkaline conditions of glycine-sodium hydroxide buffer solution (pH10), they were purified by gel filtration column chromatography (Superdex 200 pg; Amersham Pharmacia Biotech). A purified product obtained was condensed by ultrafiltration to obtain purified fucosyltransferase.

(2) Preparation of Fucosyltransferase-Immobilized Magnetic Microparticle

Fucosyltransferase obtained by purification in this Example 1(1) was presented to a biomembrane-mimicking magnetic microparticle to prepare a fucosyltransferase-immobilized magnetic microparticle. Specifically, after 1 mg of Ag-coated magnetic microparticle (ferrite microparticle; Hitachi Maxell, Ltd.) 200 nm in diameter was washed with 100 μL of ethanol 3 times, the product was reacted in 40 μL of 80 mM phosphatidyl choline linker having thiol on an alkyl chain terminus at room temperature for 16 hours to prepare a biomembrane-mimicking magnetic microparticle, as shown in FIG. 1.

Figure 2:
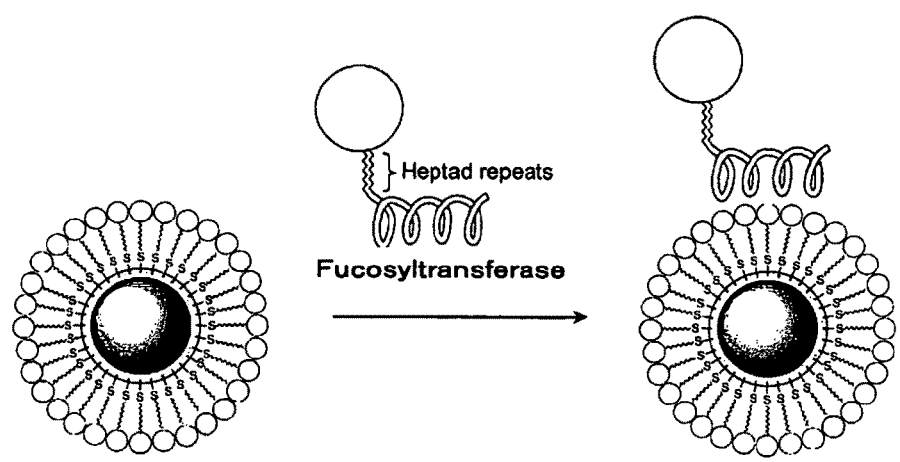
FIG. 2 is a diagram showing a process for preparing a fucosyltransferase-immobilized magnetic microparticle by immobilizing fucosyltransferase to a biomembrane mimetic magnetic microparticle via a membrane-binding peptide in Example 1(2).

Next, 100 μL (734 μg) of fucosyltransferase solution prepared by diluting purified fucosyltransferase obtained in this Example 1(1) with 100 mM Tris buffer solution (pH7.5) was added to a biomembrane-mimicking magnetic microparticle prepared in this Example 1(2) and agitated at 4° C. for 2 hours. Afterward, the biomembrane-mimicking magnetic microparticle was washed with 100 mL of 100 mM Tris buffer solution (pH7.5) 5 times to obtain a fucosyltransferase-immobilized magnetic microparticle in which fucosyltransferase was immobilized to a magnetic microparticle via a membrane-binding peptide and an organic membrane (biomimetic membrane), as shown in FIG. 2.

(3) Measurement of Fucosyltransferase Activity

[3-1: Fucosyltransferase Activity Measurement Using Lacto-N-neotetraose]

Subsequently, fucosyltransferase activity for Lacto-N-neotetraose (LNnT) as human milk oligosaccharide of a fucosyltransferase-immobilized magnetic microparticle obtained in this Example 1(2) was measured. Specifically, 1 mg of fucosyltransferase-immobilized magnetic microparticle prepared in this Example 1(2) was reacted in a mixture containing 0.5 μL of 1M manganese chloride, 2.5 μL of 200 mM guanosine 5'-2phosphoric acid-6-L-fucose (GDP-fucose), 25 μL of 40 mM LNnT, 5 μL of 1M Tris buffer solution (pH7.5) and 17 μL of ultrapure water, at room temperature for 60 minutes. The product was analyzed by saccharides analyzer (HPAEC-PAD; Dionex) every 5, 15, 30 and 60 minutes to measure fucosyltransferase activity by quantifying fucosylated pentasaccharide. A chromatograph showing measurement results, corresponding to a reaction time of 5, 15, 30 and 60 minutes, are shown in FIG. 3(*a*), (b), (c) and (d), respectively and a graph showing the data is shown in FIG. 4.

Figure 3:
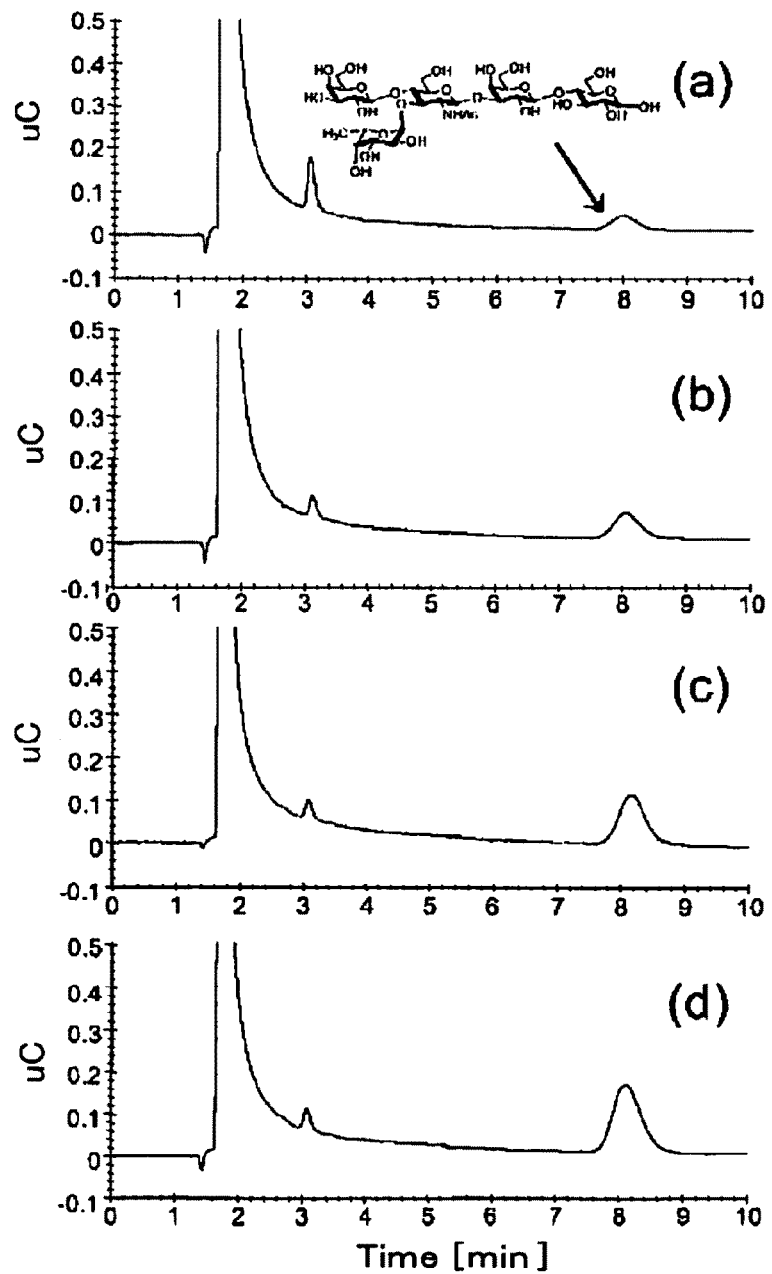
FIG. 3 is a chromatograph by the measurement of fucosyltransferase activity, using saccharides analyzer to examine fucose transfer reaction for Lacto-N-neotetraose (LNnT) of Example 1(3) [3-1] ((a), (b), (c) and (d) are chromatographs 5, 15, 30 and 60 minutes after reaction starts, respectively).
Figure 4:
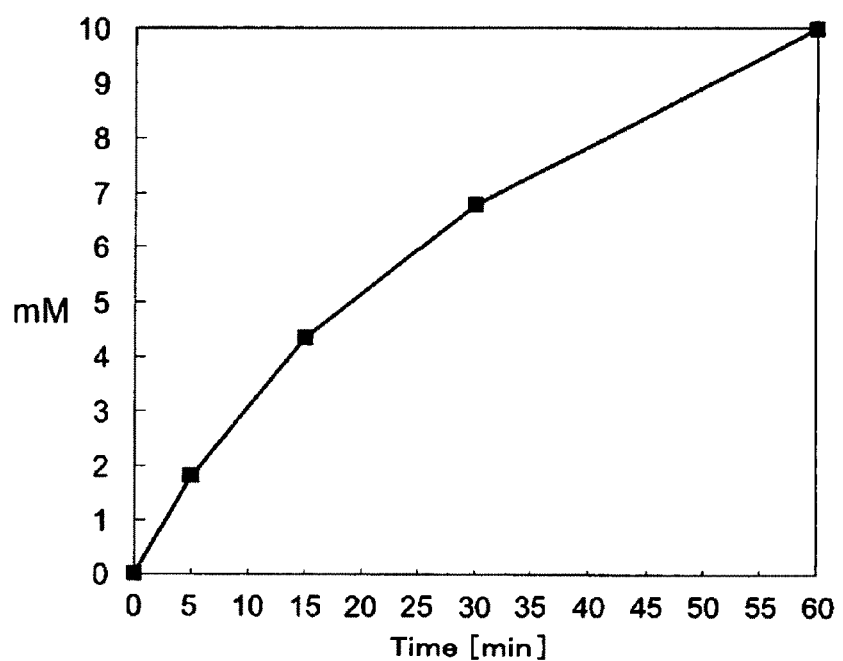
FIG. 4 is a graph showing the data of a chromatograph by the measurement of fucosyltransferase activity, using saccharides analyzer to examine fucose transfer reaction for Lacto-N-neotetraose (LNnT) of Example 1(3) [3-1].

As shown in FIG. 3, since a peak of fucosylated pentasaccharide indicated by arrow was detected and increased as time elapsed, it was confirmed that fucosyltransferase immobilized to a magnetic microparticle fucosylated LNnT. As shown in FIG. 4, it was confirmed that fucosyltransferase produced 4.32 mM pentasaccharide in 15-minute reaction. Then, the volume of pentasaccharide produced per minute was found at a high value of 2.88 U/mL, showing a high fucosyltransferase activity.

[3-2: Fucosyltransferase Activity Measurement Using O-Linked Type Sugar Amino Acid]

Figure 5:
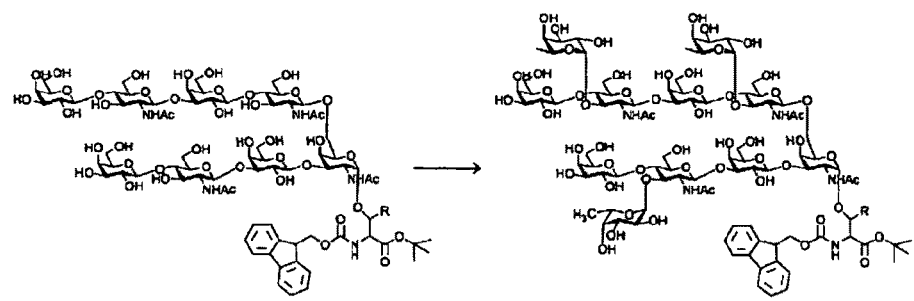
FIG. 5 is a diagram showing a process of reaction to examine fucose transfer reaction for O-linked type sugar amino acid of Example 1(3) [3-2].

Fucosyltransferase activity for O-linked type sugar amino acid of a fucosyltransferase-immobilized magnetic microparticle obtained in this Example 1(2) was measured. Specifically, 1 mg of 576 mU/mL fucosyltransferase-immobilized magnetic microparticle was reacted in a mixture containing 1 mg of O-linked type sugar amino acid (R in FIG. 5 is replaced with H; denoted as 1a) or O-linked type sugar amino acid (R in FIG. 5 is replaced with $CH_3$; denoted as 1b), 10 mM manganese chloride, 5 μL of 200 mM GDP-fucose, 5 μL of 1M Tris buffer solution (pH7.5) and 40 μL of ultrapure at room temperature for 16 hours. A reaction of O-linked type sugar amino acid to be fucosylated is shown in FIG. 5. The reaction solution was subjected to Matrix Assisted Laser Desorption/Ionization Time Of Flight mass spectrometer (MALDI-TOF-MS; Bruker) and reversed-phase high-performance liquid chromatograph (RP-HPLCHITACHI) to detect fucosylated O-linked type sugar amino acid.

Figure 6:
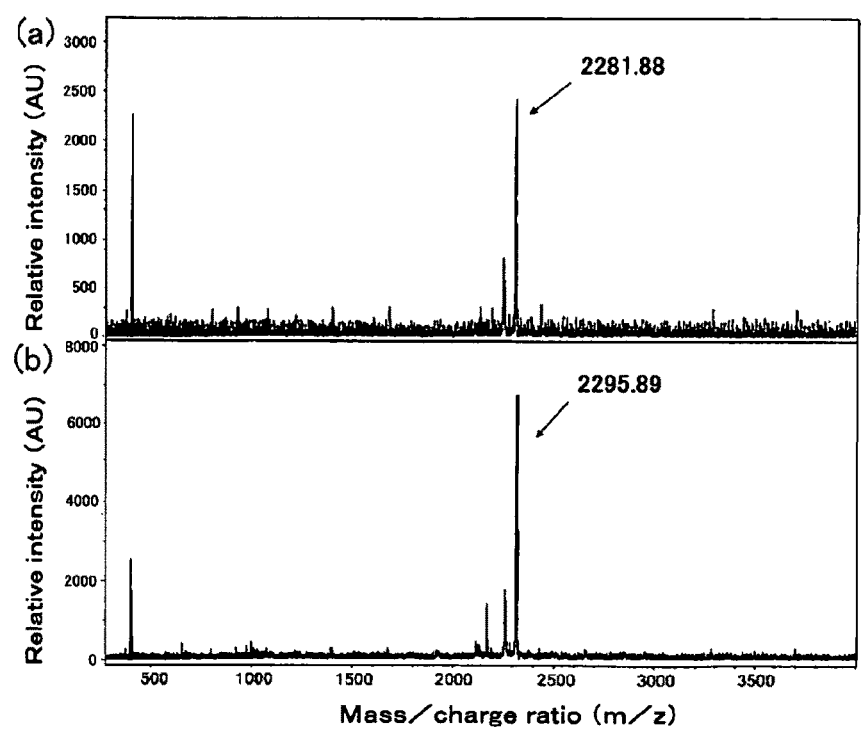
FIG. 6 is a spectral chart by the measurement of O-linked type sugar amino acid after reaction, using MALDI-TOF-MS to examine fucose transfer reaction for O-linked type sugar amino acid of Example 1(3) [3-2] ((a) and (b) are spectral charts using O-linked type sugar amino acid (1a; R=H) and O-linked type sugar amino acid (1b; R=$CH_3$), respectively).
Figure 7:
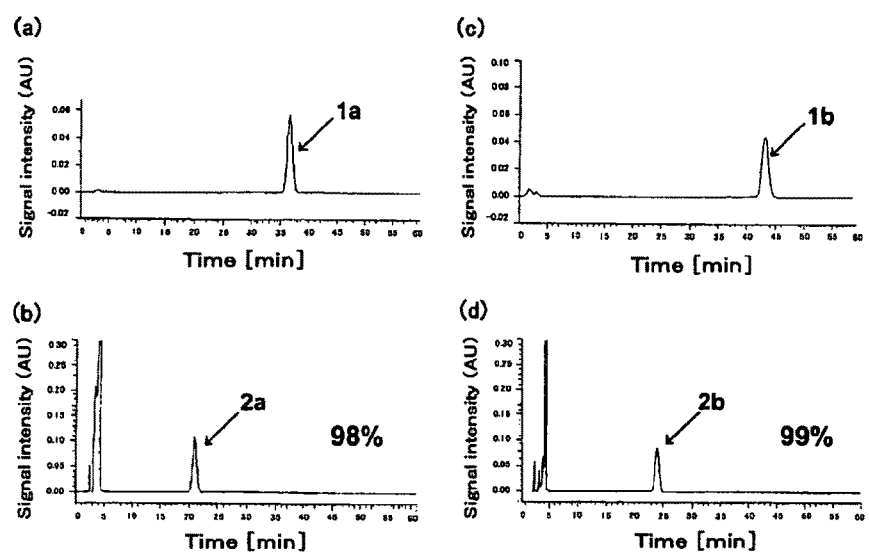
FIG. 7 is a spectral chart by the measurement of O-linked type sugar amino acid before and after reaction, using RP-HPLC to examine fucose transfer reaction for O-linked type sugar amino acid of Example 1(3) [3-2] ((a), (b), (c) and (d) are spectral charts by the measurement of O-linked type sugar amino acid (1a; R=H) before fucose transfer reaction, by the measurement of O-linked type sugar amino acid (1b; R=H) after fucose transfer reaction, by the measurement of O-linked type sugar amino acid (1a; R=$CH_3$) before fucose transfer reaction and by the measurement of O-linked type sugar amino acid (1b; R=$CH_3$) after fucose transfer reaction, respectively).

MALDI-TOF-MS was measured using 2,5-dihydroxybenzoic acid (DHB; Naruchi, K. et al., J. Org. Chem., 71, 9609-9621, 2006) as a matrix agent. A spectral chart thereof is shown in FIG. 6. Specifically, measurement results on O-linked sugar chain added to serine residues in O-linked type sugar amino acid 1a are shown in FIG. 6(*a*), and measurement results on O-linked sugar chain added to threonine residues in O-linked type sugar amino acid 1b are shown in FIG. 6(*b*). Meanwhile, RP-HPLC was measured using Inertsil ODS-3 (4.6 mM×250 mM; GL Sciences Inc.) as a reversed-phase column and methyl cyanide (pH5.8) containing 25 mM ammonium acetate (pH5.8) and 10% ammonium acetate as eluate at a flow rate of 1.0 mL/min. A spectral chart thereof is shown in FIG. 7. Specifically, measurement results before and after reaction using O-linked type sugar amino acid 1a are shown in FIGS. 7(a) and (b), respectively, and measurement results before and after reaction using O-linked type sugar amino acid 1b are shown in FIGS. 7(c) and (d), respectively.

In MALDI-TOF-MS analysis as shown in FIG. 6(a), while O-linked sugar chain added to serine residues in O-linked type sugar amino acid 1a was fucosylated (hereinafter called O-linked type sugar amino acid 2a), a peak of 2281.88 was detected. Likewise, as shown in FIG. 6(b), while O-linked sugar chain added to threonine residues in O-linked type sugar amino acid 1b was fucosylated (hereinafter called O-linked type sugar amino acid 2b), a peak of 2295.89 was detected. On the other hand, in RP-HPLC analysis as shown in FIGS. 7(a) and (b), a peak corresponding to O-linked type sugar amino acid 1a after reaction was hardly detected, but it was confirmed that a peak corresponding to fucosylated O-linked type sugar amino acid 2a was detected and 98% of O-linked type sugar amino acid 1a was fucosylated. Likewise, as shown in FIGS. 7(c) and (d), a peak corresponding to O-linked type sugar amino acid 1b after reaction was hardly detected, but it was confirmed that a peak corresponding to fucosylated O-linked type sugar amino acid 2b was detected and 99% of O-linked type sugar amino acid 1b was fucosylated. The above observations found that a fucosyltransferase-immobilized magnetic microparticle fucosylates O-linked type sugar amino acid.

[3-3: Fucosyltransferase Activity Measurement Using N-Linked Type Sugar Amino Acid]

Figure 8:
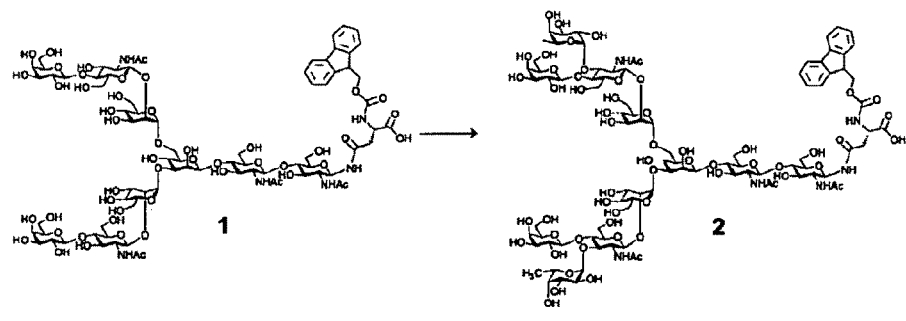
FIG. 8 is a diagram showing a process of reaction to examine fucose transfer reaction for N-linked type sugar amino acid of Example 1(3) [3-3].
Figure 9:
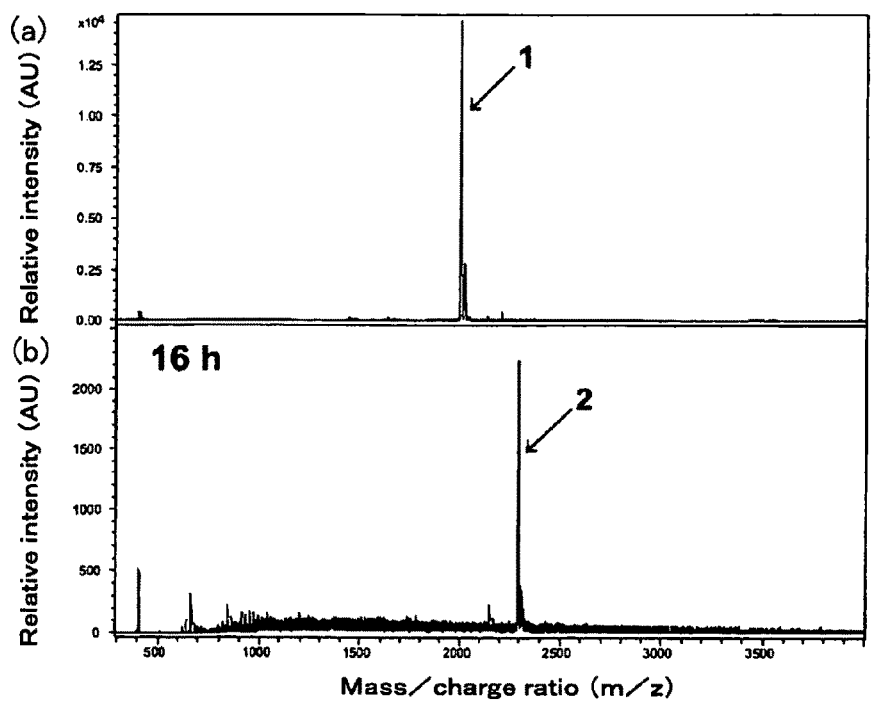
FIG. 9 is a spectral chart by the measurement of N-linked type sugar amino acid before and after reaction, using MALDI-TOF-MS to examine fucose transfer reaction for N-linked type sugar amino acid of Example 1(3) [3-3] ((a) and (b) are spectral charts by the measurement before and after fucose transfer reaction, respectively).
Figure 10:
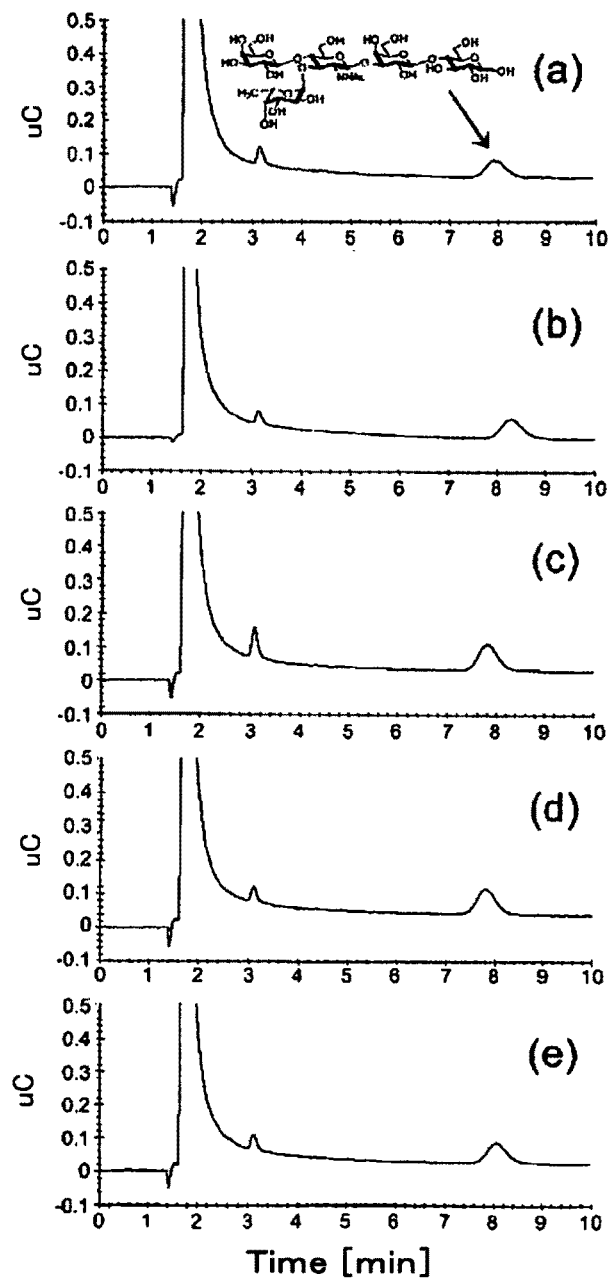
FIG. 10 is a chromatograph by the measurement of fucosyltransferase activity, using saccharides analyzer to examine a repeated use of fucosyltransferase-immobilized magnetic microparticle of Example 1(4) ((a) to (e) are chromatographs, with the number of cycles being 1 to 5, respectively).

Similarly, fucosyltransferase activity for N-linked type sugar amino acid of a fucosyltransferase-immobilized magnetic microparticle prepared in this Example 1(2) was measured. Specifically, 1 mg of 576 mU/mL fucosyltransferase-immobilized magnetic microparticle was reacted in a solution containing 5 µL of 10 mM N-linked type sugar amino acid, 0.5 µL of 1M manganese chloride, 5 µL of 200 mM GDP-fucose, 5 µL of 1M Tris buffer solution (pH7.5) and 34.5 µL of ultrapure water at room temperature for 16 hours. A reaction of N-linked type sugar amino acid to be fucosylated is shown in FIGS. 8 (1 and 2 in the figure mean N-linked type sugar amino acid and fucosylated N-linked type sugar amino acid, respectively.) Said reaction solution was subjected to MALDI-TOF-MS as in this Example 1(3) 3-2 to detect fucosylated N-linked type sugar amino acid (2 in FIG. 8). A spectral chart thereof is shown in FIG. 9. Specifically, measurement results before and after reaction are shown in FIGS. 9(a) and (b), respectively.

As shown in FIGS. 9(a) and (b), a peak corresponding to N-linked type sugar amino acid before fucosylation before reaction was detected (a), and after reaction, a peak of 2268.819 in fucosylated N-linked type sugar amino acid was detected (b). The above observations found that a fucosyltransferase-immobilized magnetic microparticle fucosylates N-linked type sugar amino acid.

From this Example 1(3) [3-1] to [3-3] described above, fucosyltransferase can be immobilized to a biomembrane-mimicking magnetic microparticle, with activity maintained, and can be used as a fucosyltransferase-immobilized magnetic microparticle.

(4) Examination of a Repeated Use and Conservation Using LNnT

Figure 11:
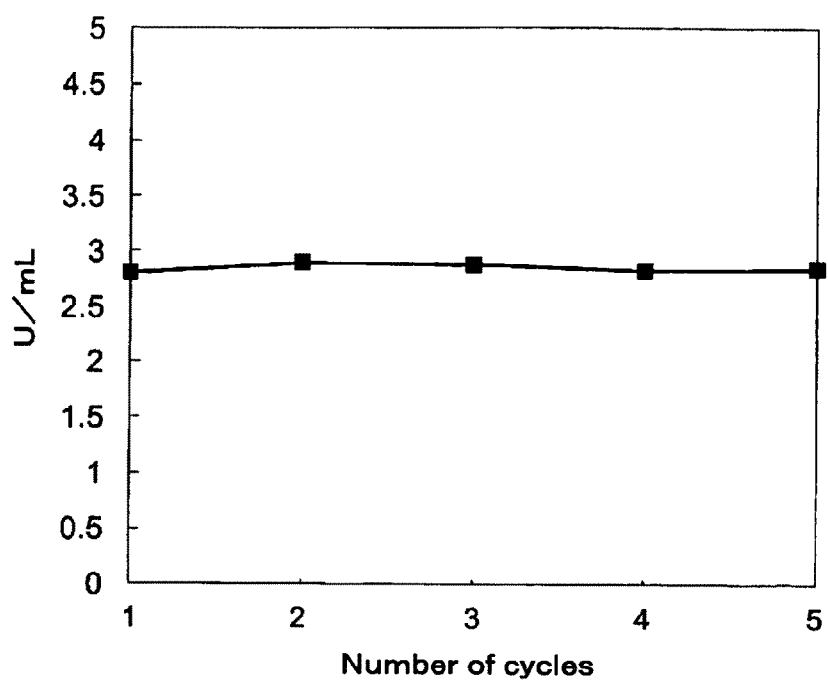
FIG. 11 is a graph showing data of chromatograph by the measurement of fucosyltransferase activity, using saccharides analyzer to examine a repeated use of fucosyltransferase-immobilized magnetic microparticle of Example 1(4).

Next, whether a fucosyltransferase-immobilized magnetic microparticle prepared in this Example 1(2) can be repeatedly used or not was discussed. Specifically, as in a method in this Example 1(3) [3-1], 1 mg of fucosyltransferase-immobilized magnetic microparticle having 576 mU/mL activity prepare in this Example 1(2) was reacted in 100 mM Tris buffer solution (0-17.5) containing 10 mM manganese chloride, 10 mM GDP-fucose and 20 mM LNnT at room temperature for 15 minutes. This was repeated 5 times, and in each step fucosyltransferase activity was measured by quantifying fucosylated pentasaccharide using saccharides analyzer (HPAEC-PAD; Dionex). In the 1st to 3rd steps, fucosyltransferase after reaction was washed with 100 µL of 100 mM Tris buffer solution (pH7.5) 5 times and another activity measurement was performed. In the 4th step, fucosyltransferase was washed with 100 µL of 100 mM Tris buffer solution (pH7.5) 5 times and washed with 100 µL of 1M sodium chloride 5 times to perform activity measurement. In the 5th step, fucosyltransferase was washed with 100 µL of 100 mM Tris buffer solution (pH7.5) 5 times and preserved at 4° C., and activity measurement was performed the following day. A chromatograph showing measurement results with numbers of cycles of 1 to 5 are shown in FIGS. 10(a) to (e), respectively, and a graph showing the data is shown in FIG. 11.

As shown in FIGS. 10(a) to (e), a peak of fucosylated pentasaccharide indicated by arrow in all cases was also confirmed. As shown in FIG. 11, it was confirmed that fucosyltransferase which was immobilized to magnetic microparticle showed no decline in activity even with a repeated use, and a level thereof was maintained. From the result of the 5th step, it was confirmed that the activity was maintained even the following day. The above observation found that a fucosyltransferase-immobilized magnetic microparticle can be repeatedly used, with fucosyltransferase activity maintained and an activity thereof conserved.

Figure 12:
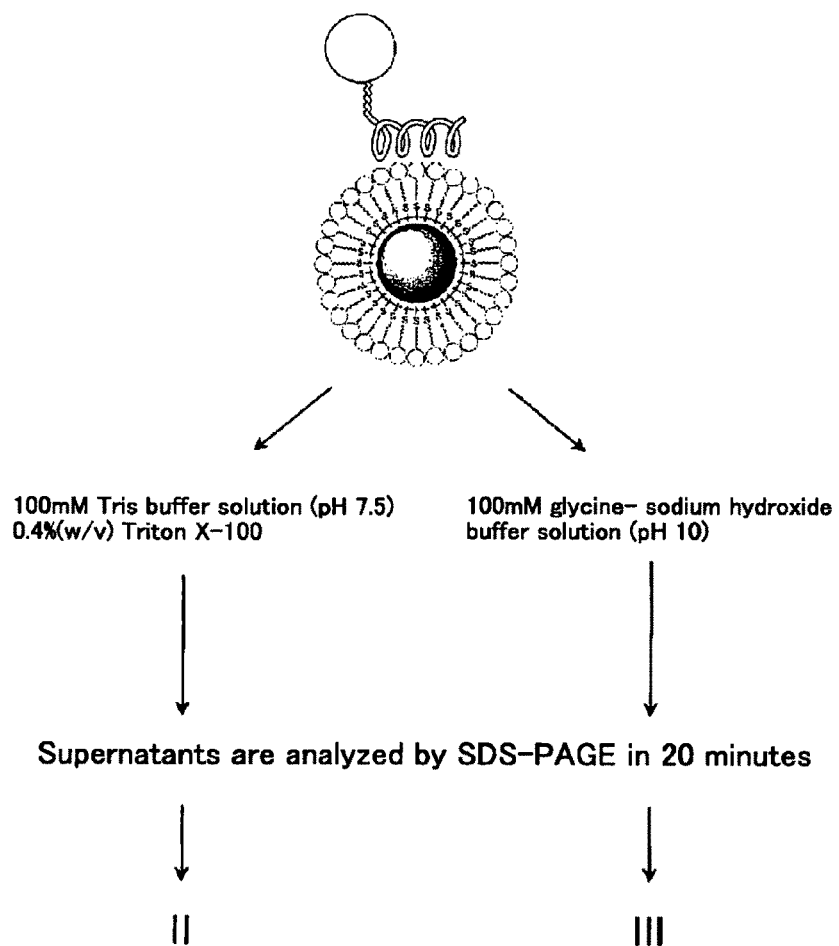
FIG. 12 is a diagram showing a process in a release test of a fucosyltransferase-immobilized magnetic microparticle of Example 1(5).
Figure 13:
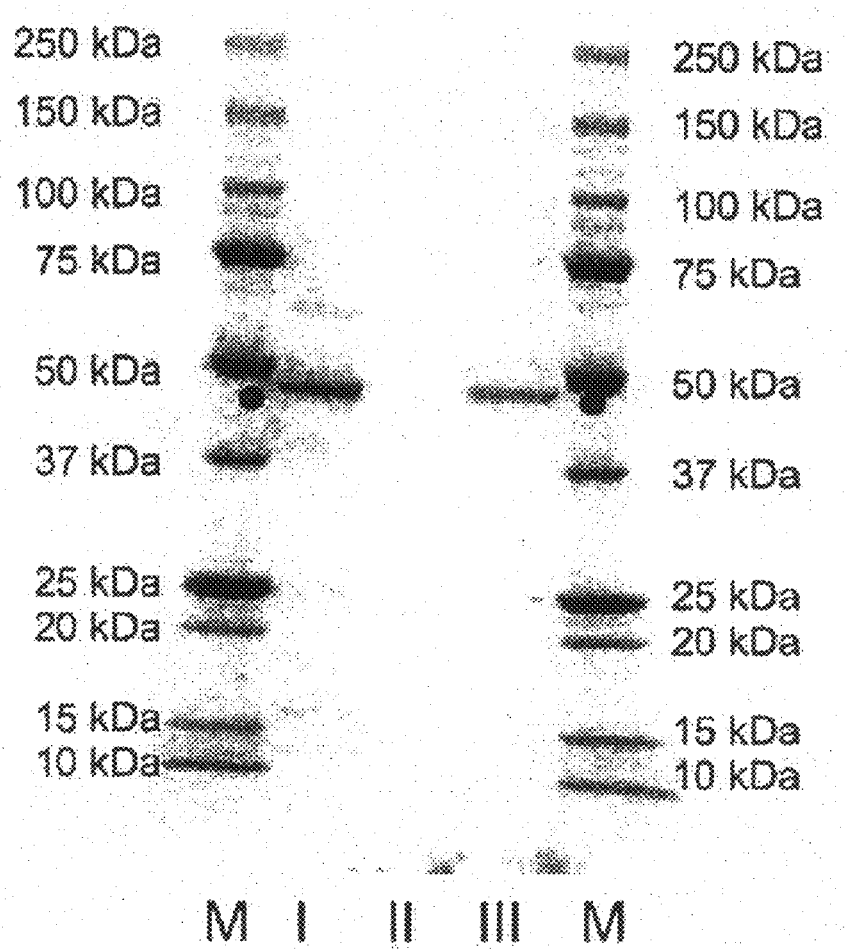
FIG. 13 is a photo showing the results of CBB dyeing after SDS-PAGE in a release test of fucosyltransferase-immobilized magnetic microparticle of Example 1(5).

(5) Release Test of Fucosyltransferase of Fucosyltransferase-Immobilized Magnetic Microparticle A release test of fucosyltransferase of fucosyltransferase-immobilized magnetic microparticle was performed. Specifically, as shown in FIG. 12, 1 mg of 576 mU/mL fucosyltransferase-immobilized magnetic microparticle prepared in this Example 1(2) was reacted in 100 mM Tris buffer solution (pH7.5) or 100 mM glycinesodium hydroxide buffer solution (pH10) containing 0.4% (w/v) Triton X-100 at room temperature for 20 minutes. Each of the reaction solutions was subjected to SDS-polyacrylamide gel electrophoresis (SDS-PAGE) and Coomasie Brilliant Blue (CBB) dyeing. The results are shown in FIG. 13 (photo). In FIG. 13, M is a lane on which molecular weight marker flowed, I is a lane on which fucosyltransferase was migrated, II is a lane on which a reaction solution treated with Tris buffer solution (pH7.5) containing Triton X-100 was migrated and III is a lane on which a reaction solution treated with glycinesodium hydroxide buffer solution (pH10) was migrated.

As shown in FIG. 13, on the lane II on which a solution treated with Tris buffer solution (pH7.5) containing Triton X-100 was migrated, electrophoretic band corresponding to fucosyltransferase was not detected, but in a solution treated with glycinesodium hydroxide buffer solution (pH10), electrophoretic band corresponding to fucosyltransferase was detected. Specifically, it was found that fucosyltransferase was not released from an immobilized biomembrane-mimicking magnetic microparticle in a surfactant such as Triton X, but released in an aqueous alkaline solution.

Herein, fucosyltransferase, as shown in this Example 1(1), under alkaline conditions of glycinesodium hydroxide buffer solution (pH10), was condensed by ultrafiltration to obtain purified fucosyltransferase without precipitation. Also, as shown in this Example 1(2), under neutrality conditions of Tris buffer solution (pH7.5), the purified fucosyltransferase solution was added to a biomembrane-mimicking magnetic microparticle to be reacted, and an α-helix structure of a membrane-binding peptide portion required for binding was induced and fucosyltransferase was successfully immobilized to a magnetic microparticle via a membrane-binding peptide.

The above observations found that fucosyltransferase was immobilized to a magnetic microparticle via a membrane-binding peptide and an organic membrane (biomimetic membrane), with activity maintained under neutrality conditions, and it was released to be solubilized under alkaline conditions, enabling a reversible use of the immobilization and release.

Example 2

Preparation of Fucosyltransferase-Immobilized Microarray and Measurement of Enzyme Activity A biomembrane-mimicking well was prepared by coating each well of a 96-hole plate with phosphatidyl choline linker having thiol in an alkyl chain terminus, and enzyme fucosyltransferase activity-immobilized microarray obtained by immobilizing fucosyltransferase to a well via a membrane-binding peptide and an organic membrane (biomimetic membrane) was measured.

(1) Preparation of Fucosyltransferase-Immobilized Microarray

100 μL of 80 mM phosphatidyl choline linker having thiol in alkyl chain terminus was added to each well of a 96-hole plate to be reacted at room temperature for 16 hours to prepare a biomembrane-mimicking well. Subsequently, after the biomembrane-mimicking well was washed with 100 μL of 100 mM Tris buffer solution (pH7.5) 5 times, 100 μL (734 μg) of fucosyltransferase solution prepared by diluting purified fucosyltransferase obtained as in Example 1(1) with 100 mM Tris buffer solution (pH7.5) was added thereto and agitated at 4° C. for 2 hours. Afterward, the biomembrane-mimicking well was washed with 100 μL of 100 mM Tris buffer solution (pH7.5) 5 times, and a fucosyltransferase-immobilized microarray was prepared via a membrane-binding peptide in fucosyltransferase and an organic membrane (biomimetic membrane).

(2) Fucosyltransferase Activity Measurement

Subsequently, fucosyltransferase activity for O-linked 4 sugar amino acid of a fucosyltransferase-immobilized microarray obtained in this Example 2(1) was measured. Specifically, a fucosyltransferase-immobilized microarray prepared in Example 1(2) was reacted in a mixture containing 1 μL of 1M manganese chloride, 5 μL of 200 mM GDP-fucose, 10 μL of 1 mM O-linked 4 sugar amino acid, 10 μL of 1M Tris buffer solution (pH7.5) and 74 μL of ultrapure water at room temperature for one hour. 1 μL of the reaction solution was subjected to MALDI-TOF-MS (Bruker), and as in Example 1(3) [3-2], 1 μL of 10 mg/mL DHB was used as a matrix agent to detect fucosylated O-linked 5 sugar amino acid. In addition, as a control, said solution was added to a fucosyltransferase nonspecific adsorption well which is not coated with phosphatidyl choline linker having thiol in alkyl chain terminus and the product was subjected to MALDI-TOF-MS. The results using a fucosyltransferase nonspecific adsorption well are shown in FIG. 14(a), and the results using a fucosyltransferase-immobilized microarray are shown in FIG. 14(b).

Figure 14:
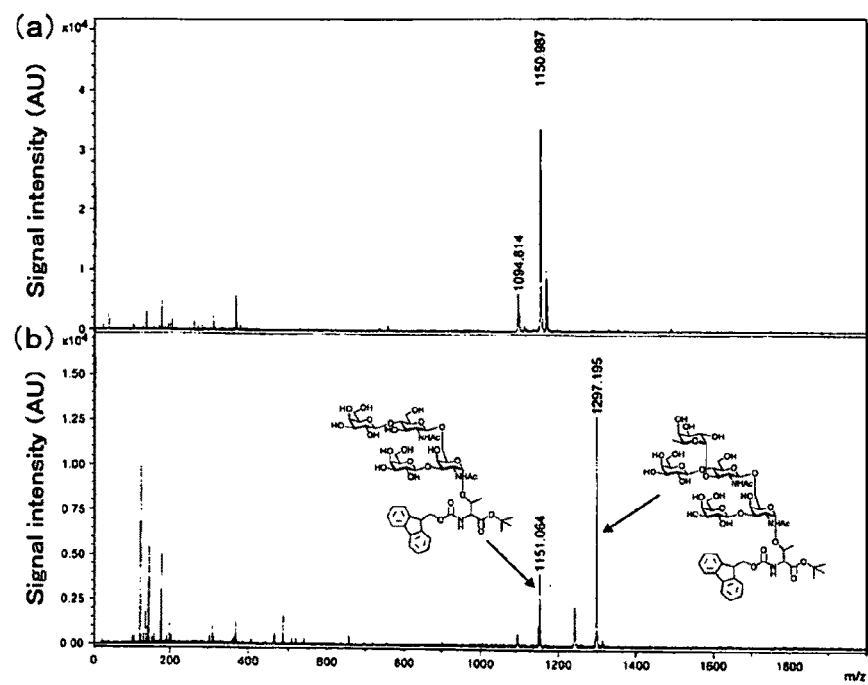
FIG. 14 is a spectral chart by the measurement of O-linked 5 sugar amino acid after reaction, using MALDI-TOF-MS to examine fucose transfer reaction for fucosyltransferase nonspecific adsorption well of Example 2(2) and O-linked 4 sugar amino acid of fucosyltransferase-immobilized microarray ((a) and (b) are spectral charts for fucosyltransferase nonspecific adsorption well and fucosyltransferase-immobilized microarray, respectively).

As shown in FIG. 14(a), in a fucosyltransferase nonspecific adsorption well, a peak of O-linked 4 sugar amino acid (peak corresponding to 1150.967) was detected, but a peak of fucosylated O-linked 5 sugar amino acid (peak corresponding to 1297.195) was not detected and no fucosyltransferase activity was confirmed. Meanwhile, as shown in FIG. 14(b), in a fucosyltransferase-immobilized microarray, a peak of O-linked 5 sugar amino acid (peak corresponding to 1297.195) was detected, and fucosyltransferase activity was confirmed. It was thus found that fucosyltransferase can be immobilized to a biomembrane-mimicking well, with activity maintained, and used as a fucosyltransferase-immobilized microarray.

The above observation found that only by dispensing a sugar chain to a probe-immobilized microarray using a probe in which a biomolecule having a membrane-binding peptide and a membrane-binding molecule having a membrane-binding peptide and biomolecule are immobilized, sugar chain trimming can be performed.

Comparative Example 1

Preparation of Sialidase Nonspecific Adsorption Magnetic Microparticle and Measurement of Enzyme Activity Using a non biomembrane-mimetic (not coating with an organic membrane) magnetic microparticle in the absence of a membrane-binding peptide, a biomolecule nonspecific adsorption magnetic microparticle was prepared and an activity thereof was measured.

(1) Preparation of Sialidase Nonspecific Adsorption Magnetic Microparticle

Specifically, 1 mg of Ag-coated magnetic microparticle 200 nm in diameter (Hitachi Maxell, Ltd.; ferrite microparticle) was firstly washed with 100 μL of ethanol 3 times, and it was not coated with phosphatidyl choline linker having thiol in an alkyl chain terminus, and 100 μL of solution (74 μg), in which sialidase (SIGMA) derived from Vivrio cholerae was diluted with 100 mM Tris buffer solution (pH7.5), was added thereto and agitated at 4° C. for 2 hours. Next, the product was washed with 100 mL of 100 mM Tris buffer solution (pH7.5) 5 times to obtain sialidase nonspecific adsorption magnetic microparticle to which sialidase was nonspecifically adsorbed.

(2) Sialidase Activity Measurement

Subsequently, sialidase activity for 4-methylumbelliferyl sialic acid of a sialidase nonspecific adsorption magnetic microparticle obtained in this Comparative Example 1(1) was measured. Specifically, after 1 mg of sialidase nonspecific adsorption magnetic microparticle prepared in this Comparative Example 1(1) was reacted in 100 mM Tris buffer solution (pH7.5) containing 2 mM calcium chloride and 20 mM 4-methylumbelliferyl sialic acid at room temperature for 10 minutes, the reaction solution was analyzed by saccharides analyzer (HPAEC-PAD; Dionex) and free sialic acid was quantified to measure sialidase activity. The activity was measured by washing the product with 100 μL of 100 mM Tris buffer solution (pH7.5) 5 times after each activity measurement was completed, and another activity measurement was repeatedly performed 3 times. The results are shown in FIG. 15.

Figure 15:
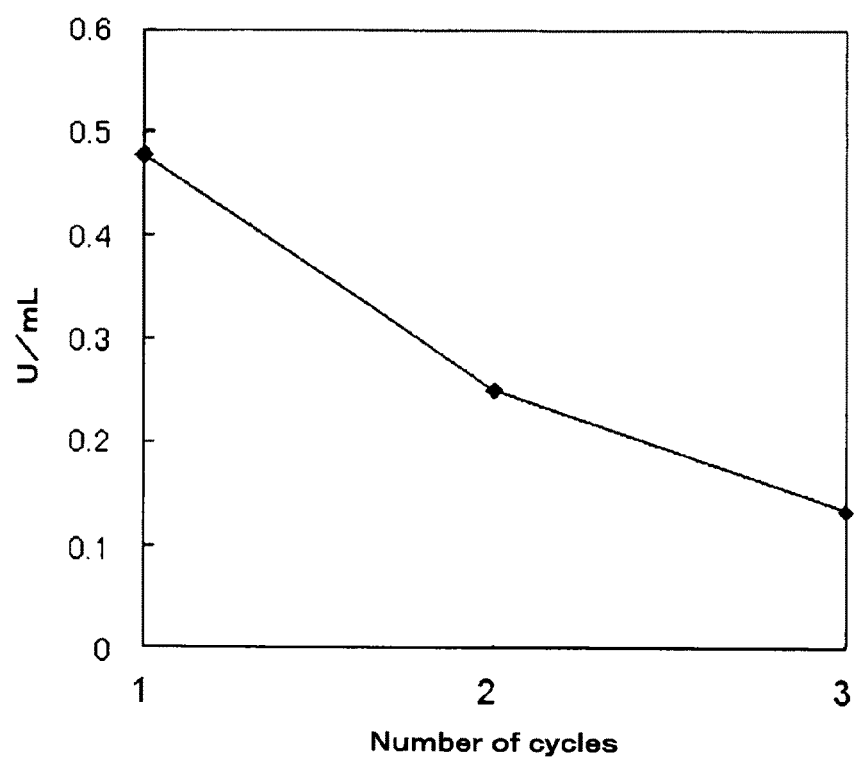
FIG. 15 is a diagram showing the results by the measurement of sialidase activity, using saccharides analyzer by a repeated use of a magnetic microparticle to which sialidase nonspecifically adsorbs in Comparative Example 1(2).

As shown in FIG. 15, sialidase nonspecific adsorption magnetic microparticle showed decline in sialidase activity due to a repeated use and the activity was not maintained. In order to confirm desorption of sialidase from magnetic microparticle, when said reaction solution was subjected to SDS-PAGE as in Example 1(5), desorption of sialidase from sialidase nonspecific adsorption magnetic microparticle was not confirmed. The above observation found that specific immobilization of a biomolecule to a magnetic microparticle via a membrane-binding peptide and an organic membrane (biomimetic membrane) maintained an activity.

Example 3

Analysis of Conformation of Membrane-Binding Peptide and Membrane Adhesiveness

Conformational analysis of membrane-binding peptide was performed in an aqueous solution or a micell solution to examine membrane adhesiveness.

Specifically, firstly, a polypeptide of 42 residues containing a membrane-binding peptide present on a C terminal side of $\alpha$-1,3 fucosyltransferase derived from *Helicobacter pylori* J99B strain was prepared by automated peptide synthesizer (APEX3962; Advanced Chem. Tech.) and measured by RP-HPLC and purified. RP-HPLC was measured as in Example 1(3) [3-2]. In conformational analysis of a membrane-binding peptide obtained by purification in an aqueous solution, a solution containing 600 μL of water (pH7.0) was used as a sample so that a membrane-binding peptide reached 62.5 μM in concentration. Meanwhile, in conformational analysis in a micell solution of membrane-binding peptide, a mixture of 240 μL of 156 μM a peptide of said 42 residues and 360 μL of 100 μM dodecylphosphocholine was used as a sample.

Next, CD analysis was performed using the samples. In CD analysis, using circular dichroism spectroscope J-820 (JASCO Corporation), CD was measured at a wavelength ranging from 190 to 250 nm by 10-time integrating. The results are shown in FIGS. 16 and 17.

Figure 16:
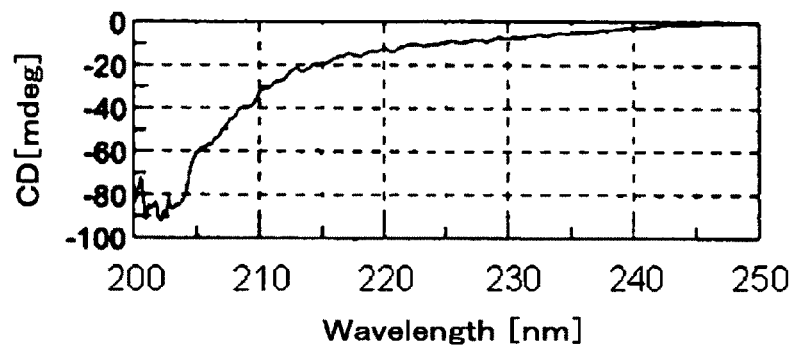
FIG. 16 is a diagram showing the results of circular dichroism (CD) analysis of a membrane-binding peptide in an aqueous solution in Example 3.
Figure 17:
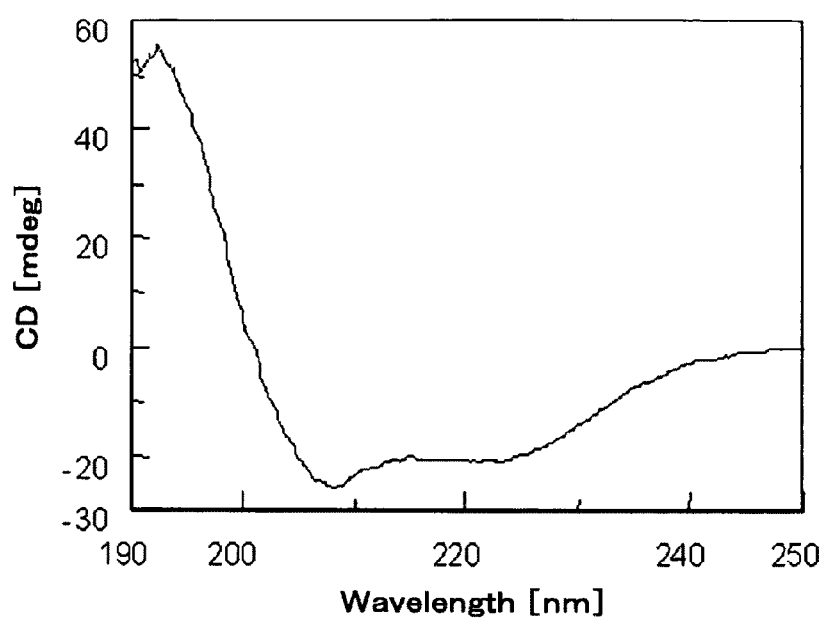
FIG. 17 is a diagram showing the results of circular dichroism (CD) analysis of a membrane-binding peptide in a micelle in which a membrane structure is mimicked in Example 3.

As shown in FIGS. 16 and 17, a membrane-binding peptide is provided with a random structure in an aqueous solution, and in membrane structure-mimicking micelle, it is provided with an $\alpha$-helix structure. The above observation found that a membrane-binding peptide was solubilized in an aqueous solution, and under conditions having membrane structure, an $\alpha$-helix structure was induced to provide membrane adhesiveness.

Example 4

Preparation of Maltose-Linked Protein-Fused Galactose Transferase (MBP-GalT)-Immobilized Magnetic Microparticle In Vitro and Measurement of Enzyme Activity Since membrane adhesiveness of a membrane-binding peptide was confirmed in Example 3, a maltose-linked protein-fused galactose transferase (MBP-GalT) was used as a biomolecule, and by presenting MBP-GalT to which a membrane-binding peptide was fused to a biomembrane-mimicking magnetic microparticle, an MBP-GalT-immobilized magnetic microparticle was prepared in vitro to measure an activity thereof.

(1) Preparation of MBP-GalT and Membrane-Binding Peptide

Figure 18:
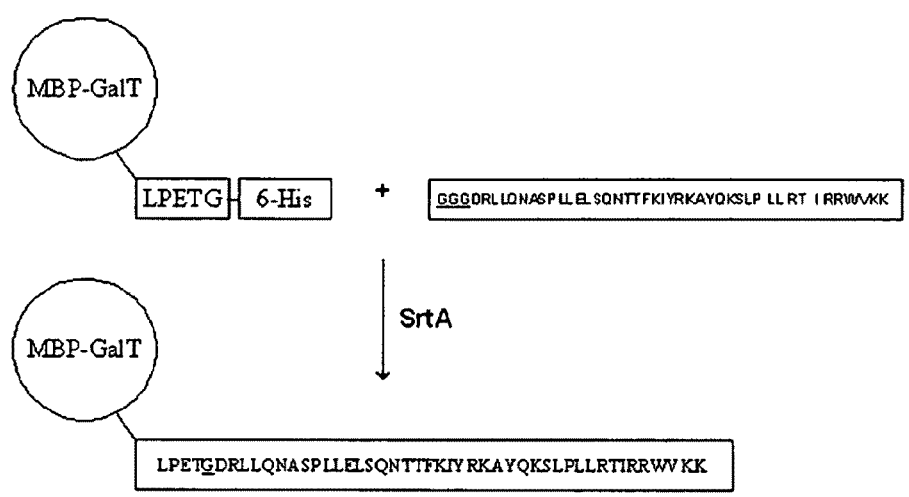
FIG. 18 is a diagram showing a process for preparing a membrane-binding peptide-fused MBP-GalT, using sortase A (SrtA) in Example 4(1).

As shown in FIG. 18, sortase A (SrtA) is an enzyme having a characteristic of binding an amino acid sequence LPETG (Leu-Pro-Glu-Thr-Gly) and a peptide having an amino acid sequence GGG (Gly-Gly-Gly; triglycine) on an N terminal. Using the enzyme, a biomolecule having an amino acid sequence LPETG on a C terminal and a membrane-binding peptide containing triglycine on an N terminal can be bound. Specifically, using SrtA, MBP-GalT having LPETG on a C terminal and a membrane-binding peptide containing triglycine on an N terminal were fused to prepare a membrane-binding peptide-fused MBP-GalT and by presenting the membrane-binding peptide-fused MBP-GalT to a biomembrane mimetic magnetic microparticle, an MBP-GalT-immobilized magnetic microparticle can be prepared.

Accordingly, MBP-GalT, and a polypeptide of 42 residues containing a membrane-binding peptide containing triglycine on an N terminal were prepared. Specifically, MBP-GalT was prepared by a method of S. Nishiguchi et al. (Susumu Nishiguchi, Shin-ichiro Nishimura., Chem. Commun., 1944-1945, 2001). A polypeptide of said 42 residues containing triglycine on an N terminal was prepared in a method as in Example 3 to be measured and purified by RP-HPLC. RP-HPLC measurement was performed at a flow rate of 10 mL/min using Inertsil ODS-3 (200 mM×250 mM; GL Sciences Inc.) as a reversed-phase column and 0.1% TFA-containing ultrapure water and 0.1% TFA-containing methyl cyanide as eluate.

(2) Preparation of MBP-GalT-Immobilized Magnetic Microparticle

MBP-GalT obtained in this Example 4(1) and a polypeptide of 42 residues containing a membrane-binding peptide containing triglycine on an N terminal were bound by SrtA, and by presenting an obtained membrane-binding peptide-fused MBP-GalT to a biomembrane mimetic magnetic microparticle, an MBP-GalT-immobilized magnetic microparticle was prepared. Specifically, 2 μL of 1.8 mM SrtA was firstly reacted in a mixture containing 1004 of 4 μM MBP-GalT obtained in this Example 4(1), 44 of polypeptide of said 42 residues containing 1 mM triglycine obtained in this Example 4(1) on an N terminal, 104 of 1M Tris-HCL buffer solution (pH7.5), 14, of 1M calcium chloride, 154 of 2M sodium chloride and 684 of ultrapure water at 37° C. for 20 hours. By transferring the reaction liquid to Microcon YM-50 (Millipore Corporation) and performing centrifugal separation at 10,000×g for 1 minute, an enzyme reaction liquid containing 504 of a membrane-binding peptide-fused MBP-GalT left in a filter was obtained, except for a polypeptide of said 42 residues containing unreacted triglycine on an N terminal.

After 1 mg of biomembrane mimetic magnetic microparticle prepared as in Example 1(2) was added to the enzyme reaction liquid and the product was agitated at 4° C. for hours, all of the solutions were removed and the biomembrane mimetic magnetic microparticle washed with 1004 of 50 mM Tris-HCL buffer solution (pH7.5) 7 times. This step can present MBP-GalT having a membrane-binding peptide on a C terminal to a biomembrane mimetic magnetic microparticle, and an MBP-GalT-immobilized magnetic microparticle, in which MBP-GalT was immobilized to a magnetic microparticle via a membrane-binding peptide and an organic membrane (biomimetic membrane), was obtained.

(3) Preparation of MBP-GalT Nonspecific Adsorption Magnetic Microparticle

As a control, a mixture of 100 μL of 4 μM MBP-GalT and 100 μL of water was added to Ag-coated magnetic microparticle which was not coated with phosphocholine linker (non biomembrane-mimetic), and by the step mentioned above, an MBP-GalT nonspecific adsorption magnetic microparticle, to which MBP-GalT adsorbed nonspecifically, was prepared.

(4) Measurement of MBP-GalT Activity of MBP-GalT-Immobilized Magnetic Microparticle and MBP-GalT Nonspecific Adsorption Magnetic Microparticle Subsequently, MBP-GalT activity for 4-methylumbelliferyl-N-acetylglucosamine (4MU-GlcNAc) of an MBP-GalT-immobilized magnetic microparticle obtained in this Example 4(2) and an MBP-GalT nonspecific adsorption magnetic microparticle obtained in this Example 4(3) was measured. Specifically, 10 µL of 1M manganese chloride, 25 µL of 25 mM uridine 5'-2phosphoric acid-α-D-galactose (UDP-Gal), 200 µL of 2.5 mM 4MU-GlcNAc, 50 µL of 1M Tris-HCL buffer solution (pH7.5) and 1 µL of 10% (w/v) Triton X-100 were mixed with 714 µL of ultrapure water to prepare a substrate solution. The substrate solution was added to 1 mg of MBP-GalT-immobilized magnetic microparticle and 1 mg of MBP-GalT nonspecific adsorptions magnetic microparticle prepared in the Examples 4(2) and (3), respectively, each by 50 µL to be reacted at room temperature for 30 minutes. 50 µL of each reaction liquid was diluted in 450 mL of ultrapure water and analyzed by RP-HPLC. Measurement results of an MBP-GalT nonspecific adsorption magnetic microparticle as a control are shown in FIG. 19(a), and measurement results of an MBP-GalT-immobilized magnetic microparticle via a membrane-binding peptide are shown in FIG. 19(b).

Figure 19:
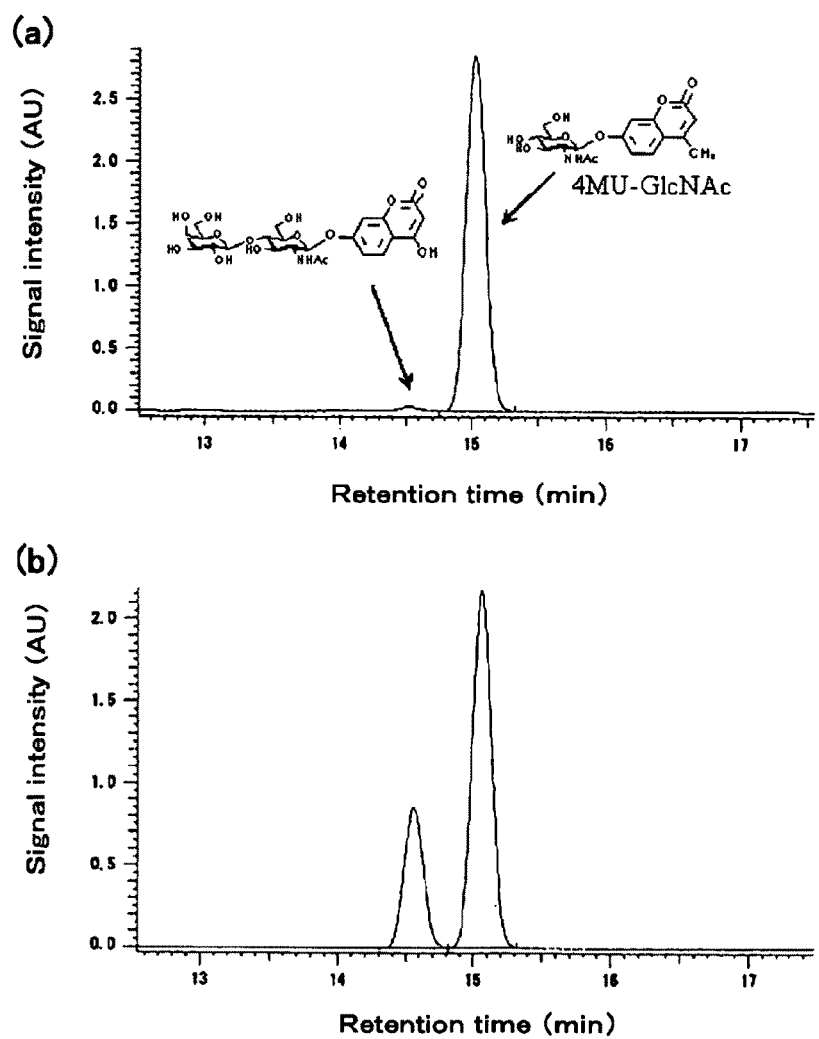
FIG. 19 is a spectral chart measured by RP-HPLC after galactose transfer reaction of 4-methylumbelliferyl-N-acetylglucosamine (4MU-GlcNAc) by the measurement of activity of a maltose-linked protein-fused galactose transferase (MBP-GalT)-immobilized magnetic microparticle of Example 4(4) ((a) and (b) are spectral charts measured by MBP-GalT nonspecific adsorption magnetic microparticle and MBP-GalT-immobilized magnetic microparticle, respectively).

As shown in FIG. 19(a), in an MBP-GalT nonspecific adsorption magnetic microparticle, a peak corresponding to 4MU-GlcNAc was mainly detected, and a peak corresponding to 4MU-GlcNAc-(β1, 4)-Gal in which galactose was bound to 4MU-GlcNAc was hardly detected, resulting in confirmation of no enzyme activity of MBP-GalT. Meanwhile, as shown in FIG. 19(b), an MBP-GalT-immobilized magnetic microparticle detected a peak corresponding to 4MU-GlcNAc and a peak corresponding to 4MU-GlcNAc-(β1, 4)-Gal, and enzyme activity of MBP-GalT was confirmed. The above observation found that MBP-GalT to which a membrane-binding peptide was fused can be immobilized to a biomembrane mimetic magnetic microparticle, with activity maintained, and the MBP-GalT can be used as an MBP-GalT-immobilized magnetic microparticle.

From the above observation, according to Examples 1 and 4, fucosyltransferase having a membrane-binding peptide and MBP-GalT to which a membrane-binding peptide was fused can be immobilized to a biomembrane mimetic magnetic microparticle and each activity was confirmed, resulting in a possibility of using not only a biomolecule having a membrane-binding peptide, but also a membrane-binding molecule to which a membrane-binding peptide was fused. Then, it was found that as long as a biomolecule is immobilized to a magnetic microparticle via a membrane-binding peptide and an organic membrane (biomimetic membrane), a biomolecule-immobilized magnetic microparticle, which is immobilized with biomolecule activity maintained, can be obtained.

Comparative Example 2

Figure 20:
FIG. 20 is a diagram showing a process for preparing an MBP-GalT-immobilized SEPHAROSE™ resin in Comparative Example 2(1).

(1) Preparation of MBP-GalT-Immobilized SEPHAROSE™ Resin In Vitro and Measurement of Enzyme Activity (1) Preparation of MBP-GalT-immobilized SEPHAROSE™ resin in vitro By immobilizing MBP-GalT used in Example 4 to cyanobromid (BrCN) activated SEPHAROSE™ 4B, MBP-GalT-immobilized SEPHAROSE™ resin was prepared in vitro (FIG. 20). Specifically, 500 µL, of 2 µM MBP-GalT obtained by a method as in Example 4(1) (Nishiguchi, S. et al., Chem. Commun, 1944-1945, 2001) was reacted in 100 mM Tris buffer solution (pH8) containing 0.3 mL of BrCN activated SEPHAROSE™ 4B (GE Healthcare Japan Corporation) at 4° C. for 16 hours. The reaction liquid was subjected to centrifugal separation at 1000×g in ULTRAFREE-MC 0.45 µmb Filter-Unit (Millipore Corporation) for 3 minutes to obtain MBP-GalT-immobilized SEPHAROSE™ resin.

(2) MBP-GalT Activity Measurement

Figure 21:
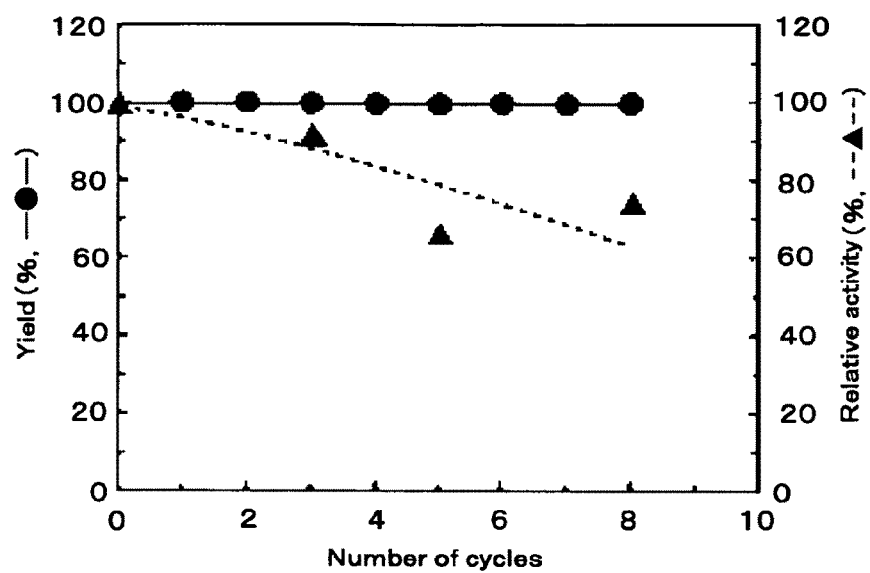
FIG. 21 is a diagram showing the results of galactose transferase activity by a repeated use of an MBP-GalT-immobilized SEPHAROSE™ resin in Comparative Example 2(2).

Subsequently, MBP-GalT activity for UDP-Gal as glycosyl donor of an MBP-GalT-immobilized SEPHAROSE™ resin obtained in this Comparative Example 2(1) was measured. Specifically, after 0.3 mL of MBP-GalT-immobilized SEPHAROSE™ resin having 0.2 U activity prepared in this Comparative Example 2(1) was reacted in 50 mM Hepes (HEPES) buffer solution (pH7.5) containing 13 mM UDP-Gal and 10 mM receptor in which 2-aminopyridyl-N-acetylglucosamine was bound to polyacrylamide polymer at 37° C. for 24 hours, the product was fractionated by Sephadex G-25 (GE Healthcare Japan Corporation) to measure enzyme activity. The enzyme activity was repeatedly measured 8 times. The activity measurement results are shown in FIG. 21. In the figure, the yield (%, ●) shows the percentage of a compound, in which galactose was introduced to polyacrylamide polymer bound by N-acetylglucosamine as a receptor (conversion rate). Meanwhile, the relative activity (%, ▲) shows relative value obtained by defining the initial enzyme activity value as 100%.

As shown in FIG. 21, as MBP-GalT activity was repeatedly measured, enzyme activity declined and activity was not maintained. The above observation found that without intervention by a membrane-binding peptide and an organic membrane (biomimetic membrane), MBP-GalT immobilized to a carrier cannot maintain enzyme activity.

Example 5

Preparation of O-Linked Glycopeptide (Mucin-Type Peptide) Immobilized Magnetic Microparticle In Vitro and Confirmation of Immobilization O-linked glycopeptide (mucin-type peptide) as a membrane-binding peptide (glycopeptide) having sugar chain was used as a biomolecule to prepare a membrane-binding peptide-fused O-linked glycopeptide incorporating a polypeptide of 42 residues containing a membrane-binding peptide on a C terminal of the O-linked glycopeptide in vitro, and by presenting the membrane-binding peptide-fused O-linked glycopeptide to a biomembrane-mimicking magnetic microparticle, O-linked glycopeptide-immobilized magnetic microparticle was prepared and an activity thereof was measured.

(1) Preparation of O-Linked Glycopeptide and Membrane-Binding Peptide

O-linked glycopeptide (mucin-type peptide) was prepared according to a method described in Naruchi, K. et al., J. Org. Chem., 71, 9609-9621, 2006, and a polypeptide of 42 residues containing a membrane-binding peptide containing triglycine on an N terminal was prepared by a method as in Example 3 and measured and purified by RP-HPLC by a method as in Example 4(1).

(2) Preparation of O-Linked Glycopeptide-Immobilized Magnetic Microparticle

Figure 22:
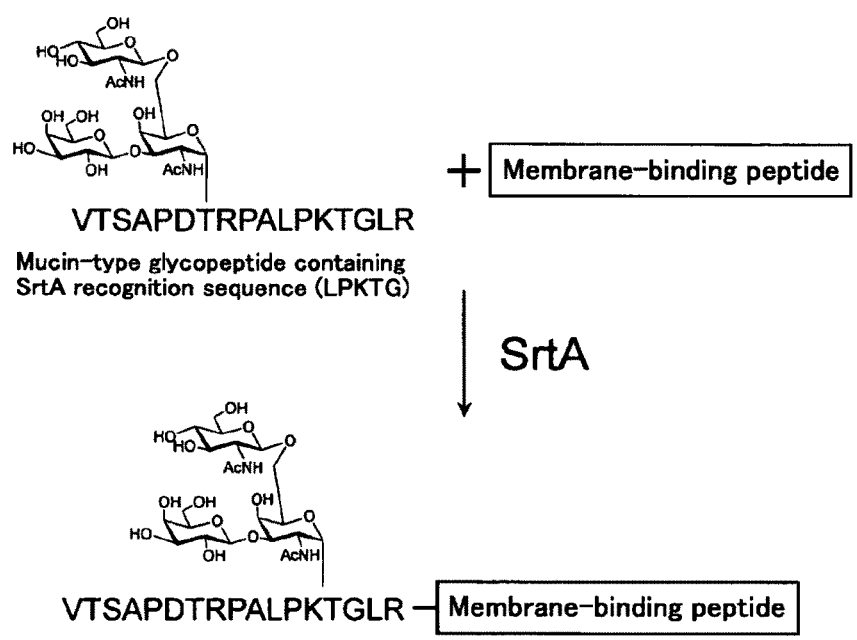
FIG. 22 is a process for preparing a membrane-binding peptide-fused 0-linked glycopeptide of Example 5(2). LPKTG is SEQ ID NO: 10. VTSAPDTRPALPKTGLR is SEQ ID NO: 11.

O-linked glycopeptide (containing SrtA recognition sequence on a C terminal) obtained in this Example 5(1) and a polypeptide of 42 residues containing a membrane-binding peptide containing triglycine on N terminal were bound by SrtA, and by presenting a membrane-binding peptide-fused O-linked glycopeptide obtained to a biomembrane mimetic magnetic microparticle, O-linked glycopeptide-immobilized magnetic microparticle was prepared. Specifically, 1 µL of 1.8 mM SrtA was reacted in a mixture containing 2.54, of 10 mM O-linked glycopeptide obtained in this Example 5(1), 2.5 µL of polypeptide of said 42 residues containing 10 mM triglycine on an N terminal obtained in this Example 5(1), 2.5

µL of 1M Tris buffer solution (pH7.5), 2.54, of 100 mM calcium chloride, 2.5 µL of 3M sodium chloride and 35.54, of ultrapure water at 37° C. for 20 hours. The reaction liquid was transferred to Microcon YM-10 (Millipore Corporation) and subjected to centrifugal separation at 14,000×g for 20 minutes to remove SrtA and obtain a peptide mixture by filtration. The mixture was measured by RP-HPLC by a method as in Example 4(1) and purified to obtain a membrane-binding peptide-fused O-linked glycopeptide. The process for preparing a membrane-binding peptide-fused O-linked glycopeptide is shown in FIG. 22.

After 1 mg of biomembrane mimetic magnetic microparticle prepared by a method as in Example 1(2) was added to membrane-binding peptide-fused O-linked glycopeptide obtained and agitated at 4° C. for 2 hours, all of the solutions were removed and biomembrane mimetic magnetic microparticle was washed with 100 µL of 50 mM Tris buffer solution (pH7.5) 5 times. The step can present O-linked glycopeptide having a membrane-binding peptide on a C terminal to a biomembrane mimetic magnetic microparticle to obtain O-linked glycopeptide-immobilized magnetic microparticle in which O-linked glycopeptide was immobilized to magnetic microparticle via a membrane-binding peptide and an organic membrane (biomimetic membrane).

(3) Preparation of O-Linked Glycopeptide-Immobilized Ag-Coated Magnetic Microparticle As a control, a membrane-binding peptide-fused O-linked glycopeptide was presented to Ag-coated magnetic microparticle which was not coated with phosphocholine linker (non biomembrane-mimetic) to prepare O-linked glycopeptide-immobilized Ag-coated magnetic microparticle. Specifically, after 1 mg of Ag-coated magnetic microparticle 200 nm in diameter washed with 100 µL of ethanol 3 times (Hitachi Maxell, Ltd.; ferrite microparticle) was added to membrane-binding peptide-fused O-linked glycopeptide obtained in this Example 5(2) at 4° C. for 2 hours, all of the solutions were removed and Ag-coated magnetic microparticle was washed with 100 µL of 50 mM Tris buffer solution (pH7.5) 5 times.

Figure 23:
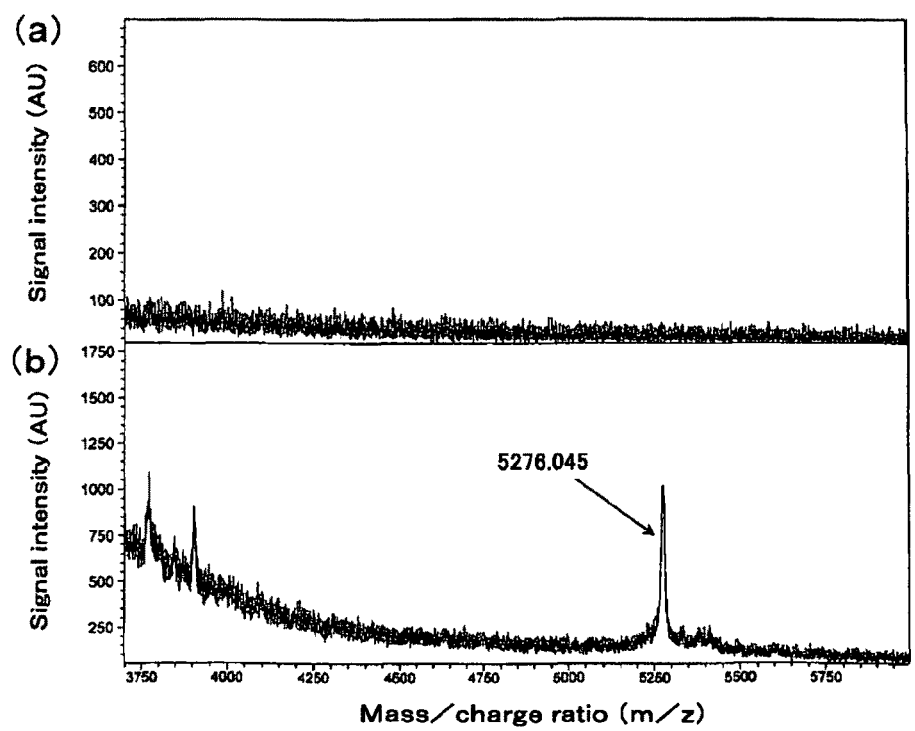
FIG. 23 is a spectral chart measured by MALDI-TOF-MS to confirm the immobilization of a membrane-binding peptide-fused O-linked glycopeptide in an O-linked glycopeptide-immobilized magnetic microparticle of Example 5(4) and an O-linked glycopeptide-immobilized Ag-coated magnetic microparticle ((a) and (b) are spectral charts measured by O-linked glycopeptide-immobilized Ag-coated magnetic microparticle and O-linked glycopeptide-immobilized magnetic microparticle, respectively).

(4) Confirmation of Immobilization of Membrane-Binding Peptide-Fused O-Linked Glycopeptide in O-Linked Glycopeptide-Immobilized Magnetic Microparticle and O-Linked Glycopeptide-Immobilized Ag-Coated Magnetic Microparticle Whether a membrane-binding peptide-fused O-linked glycopeptide is immobilized in O-linked glycopeptide-immobilized magnetic microparticle and O-linked glycopeptide-immobilized Ag-coated magnetic microparticle or not was confirmed. Specifically, O-linked glycopeptide-immobilized magnetic microparticle and O-linked glycopeptide-immobilized Ag-coated magnetic microparticle prepared in the Examples 5(2) and (3) were taken in a small volume by tip end and spotted on a target for MALDI-TOF-MS. 1 µL of 10 mg/mL DHB was mixed therewith and dried, and the product was measured by MALDI-TOF-MS. The results are shown in FIG. 23.

As shown in FIG. 23(a), in O-linked glycopeptide-immobilized Ag-coated magnetic microparticle, a peak corresponding to membrane-binding peptide-fused O-linked glycopeptide was not confirmed, thereby confirming no immobilization of membrane-binding peptide-fused O-linked glycopeptide. Meanwhile, as shown in FIG. 23(b), a peak corresponding to membrane-binding peptide-fused O-linked glycopeptide (peak of 5276.045) was confirmed in O-linked glycopeptide-immobilized magnetic microparticle, thereby confirming immobilization of membrane-binding peptide-fused O-linked glycopeptide.

Example 6

Discussion as Antibody Separating Agent Using O-Linked Glycopeptide-Immobilized Magnetic Microparticle Using an antibody which specifically recognizes O-linked glycopeptide immobilized to a biomembrane-mimicking magnetic microparticle via a membrane-binding peptide and an organic membrane (biomimetic membrane), a possible use as antibody separating agent was discussed. Specifically, 1004 of solution obtained by diluting primary antibody VU-3C6 (Exalpha Biologicals) which recognizes mucin-type glycopeptide MUC1 containing 50 mM Tris buffer solution (pH7.5) 1000 times was added to a mixture containing O-linked glycopeptide-immobilized magnetic microparticle prepared in a method as in Example 5(2) and Fetal Bovine Serum (FBS) whose final concentration was 1% and reacted at room temperature for one hour. Thereafter, O-linked glycopeptide-immobilized magnetic microparticle was washed with 1004 of 100 mM Tris buffer solution (pH7.5) containing 0.2M NaCl and 0.05% Tween 5 times to be collected, and 100 µL of 1000-time diluted HRP conjugate-mouse monoclonal antibody (Kirkegaard & Perry Laboratories) was mixed therewith and reacted at room temperature for one hour.

After reaction, O-linked glycopeptide-immobilized magnetic microparticle was again washed with 1004 of 100 mM Tris buffer solution (pH7.5) containing 0.2M NaCl and 0.05% Tween 5 times to be collected, and 100 µL of TMB-Microwell-Peroxidase-Substrate-System reagent (Kirkegaard & Perry Laboratories) was added thereto. Thereafter, an absorbance at 450 nm was measured and color development was confirmed. As a control, using a step as described above, color development was confirmed in a biomembrane mimetic magnetic microparticle coated with phosphocholine linker prepared by a method as in Example 1(2) and O-linked glycopeptide-immobilized Ag-coated magnetic microparticle prepared by a method as in Example 5(3). The results are shown in FIG. 24 (photo).

Figure 24:
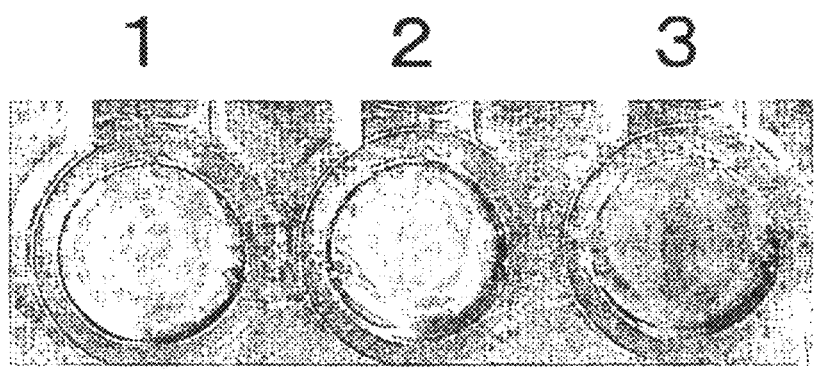
FIG. 24 is a photo showing color development of O-linked glycopeptide-immobilized magnetic microparticle, biomembrane mimetic magnetic microparticle and O-linked glycopeptide-immobilized Ag-coated magnetic microparticle, using assay kit to examine use of O-linked glycopeptide-immobilized magnetic microparticle of Example 6 as antibody separating agent ((a), (b) and (c) are photos used by biomembrane mimetic magnetic microparticle, O-linked glycopeptide-immobilized Ag-coated magnetic microparticle and O-linked glycopeptide-immobilized magnetic microparticle, respectively).

As shown in FIGS. 24 (a) to (c), while a case of O-linked glycopeptide-immobilized magnetic microparticle showed strong color development, cases of biomembrane mimetic magnetic microparticle and O-linked glycopeptide-immobilized Ag-coated magnetic microparticle used as a control hardly showed color development. The above observations found that O-linked glycopeptide-immobilized magnetic microparticle can be used as a practical antibody separating agent.

Example 7

Preparation of O-Linked Glycopeptide-Immobilized Microarray

Since it was found that O-linked glycopeptide-immobilized carrier can be used as a practical antibody separating agent in Example 6,0-linked glycopeptide-immobilized microarray was prepared.

(1) Preparation of Substrate of O-Linked Glycopeptide-Immobilized Microarray

In order to prepare substrate of O-linked glycopeptide-immobilized microarray, after gold-coated chip was coated with phosphocholine linker by a method as in Example 2(1), the chip was fixed to a glass slide to be engaged into MTP- Slide-Adaptor II (Bruker). A portion spotted was washed with a mixture containing 5 μL of ethanol, 5 μL of ultrapure water and 5 μL of 50 mM Tris buffer solution (pH7.5) 5 times to prepare a substrate of O-linked glycopeptide-immobilized microarray.

(2) Preparation of O-Linked Glycopeptide-Immobilized Microarray and Confirmation of Immobilization 5 μL of 500 μM membrane-binding peptide-fused O-linked glycopeptide prepared by a method as in Example 5(1) was spotted on a substrate of O-linked glycopeptide-immobilized microarray prepared in this Example 7(1). 5 minutes after the product was allowed to stand, it was washed with 54 of 50 mM Tris buffer solution (pH7.5) 5 times. As a result of the measurement using MALDI-TOF-MS by a method as in Example 1(3) [3-2], immobilization of a membrane-binding peptide-fused O-linked glycopeptide was confirmed. O-linked glycopeptide-immobilized microarray is shown in FIG. 25 (photo), and a spectral chart by the measurement using MALDI-TOF-MS is shown in FIG. 26.

Figure 25:
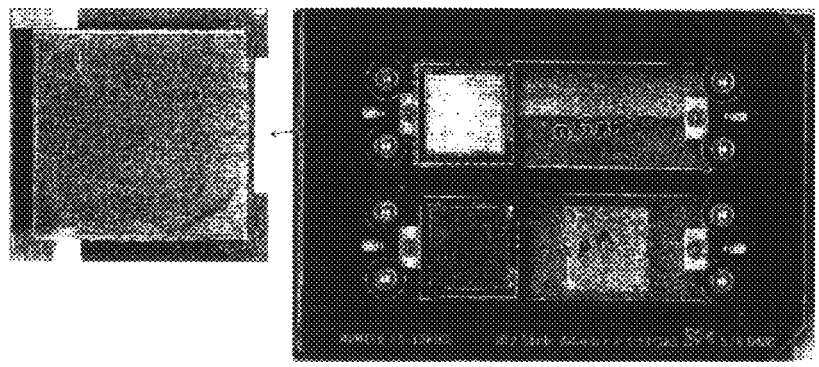
FIG. 25 is a photo showing O-linked glycopeptide-immobilized microarray prepared in Example 7(2).
Figure 26:
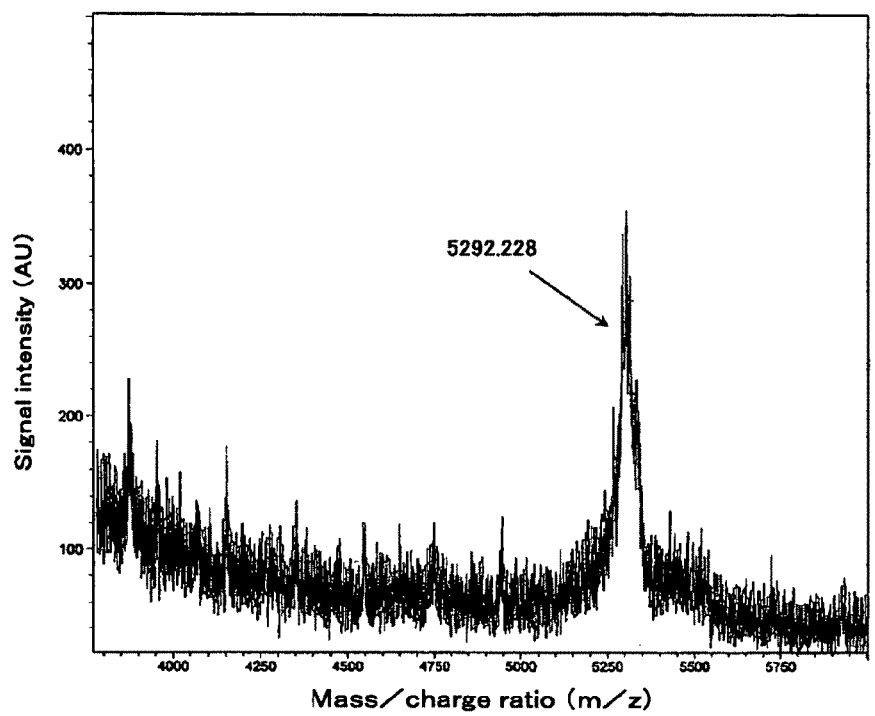
FIG. 26 is a spectral chart showing membrane-binding peptide-fused O-linked glycopeptide immobilization measured by MALDI-TOF-MS in O-linked glycopeptide-immobilized microarray prepared in Example 7(2).

As shown in FIGS. 25 and 26, a peak corresponding to membrane-binding peptide-fused O-linked glycopeptide (peak of 5292.228) was confirmed in O-linked glycopeptide-immobilized microarray prepared, and immobilization of membrane-binding peptide-fused O-linked glycopeptide was found.

Example 8

Preparation of Membrane-Binding Peptide-Fused Biomolecule In Vivo

A biomolecule to which membrane-binding peptide was fused, which can be immobilized to a biomembrane-mimicking magnetic microparticle, was prepared in vivo. Specifically, using sialidase NEU2 derived from as an enzyme which hydrolyzes sialic acid present on sugar chain terminal as a biomolecule, a membrane-binding peptide-fused sialidase incorporating a polypeptide of 42 residues containing a membrane-binding peptide on C terminal of the sialidase NEU2 derived from human was prepared in vivo.

A primer was designed as follows, so that the polypeptide of the above 42 residues is cut from a vector used in preparing α-1,3 fucosyltransferase derived from *Helicobacter pylori* J99B strain having the polypeptide of the said 42 residues in Example 1(1), and a sequence thereof was amplified under the following conditions by PCR method.

Primer;

```
5'CAAAGCTTGATCGCCTTTTACAAAACGCT3'  (SEQ ID NO: 3)

5'CTGTGACTGGTGAGTACTCAACCAAGT  (SEQ ID NO: 4)
```

Reaction Condition;

30 cycles, each composed of a step at 95° C. for 30 seconds, a step at 55° C. for 30 seconds and a step at 68° C. for 1 minute and 30 seconds Sialidase NEU2 was cloned from cDNA derived from small intestines (Invitrogen) to obtain a vector in which sialidase NEU2 was constructed. (Monti E. et al., J.B.C., 279, 3169-3179, 2004).

Fragments encoding the polypeptide of the above 42 residues and the vector, in which the above sialidase NEU2 was constructed, were treated with restriction enzymes of NdeI and BamHI to construct an expression vector of sialidase NEU2, in which a membrane-binding peptide was fused to a C terminal. The vector was transformed to *E. coli* JM109 strain to prepare *E. coli* variant. After the product was cultured on LB agar medium at 37° C. overnight, a colony was inoculated on 2.5 mL of LB medium to be cultured at 37° C. overnight. After the culture solution was subcultured on 50 mL of LB medium and was cultured at 37° C. for 2 hours so that an absorbance (OD600) at 600 nm reached 0.7, isopropylthiogalactoside (IPTG) was added thereto so that a final concentration thereof reached 0.25 mM and cultured at 20° C. for 20 hours.

The culture solution was subjected to centrifugal separation at 10,000×g for 20 minutes to collect bacterial cells, and suspended in 5 mL of 25 mM Tris buffer solution (pH8.0) containing 1 mM mercaptoethanol and 10% (w/v) glycerol, and ultrasonic crushing of bacterial cells was performed 5 times for 2 minutes each under cooling by ultrasonic crusher. After the product was again subjected to centrifugal separation at 10,000×g for 10 minutes, supernatants were collected and subjected to SDS-PAGE, the activity was measured to confirm membrane-binding peptide-fused sialidase. Subsequently, after supernatants collected were subjected to Ni column (His Trap FF; Amersham Pharmacia Biotech) under alkaline conditions (pH 8 to 10), they were condensed by ultrafiltration under alkaline conditions (pH 8 to 10) to obtain purified membrane-binding peptide-fused sialidase.

Example 9

Preparation of MBP-GalT-Immobilized Magnetic Microparticle In Vivo and Measurement of Enzyme Activity Since preparation of a biomolecule in which membrane-binding peptide was fused in vivo in Example 8 was confirmed, using MBP-GalT as a biomolecule, a membrane-binding peptide-fused MBP-GalT incorporating a polypeptide of 42 residues containing membrane-binding peptide on C terminal of the MBP-GalT was prepared in vivo and by presenting the membrane-binding peptide-fused MBP-GalT to a biomembrane-mimicking magnetic microparticle, MBP-GalT-immobilized magnetic microparticle was prepared and an activity thereof was measured.

(1) Preparation of Membrane-Binding Peptide-Fused MBP-GalT In Vivo

Fragments encoding a polypeptide of 42 residues containing membrane-binding peptide prepared in Example 8 and a vector in which MBP-GalT was constructed (Susumu Nishiguchi, Shin-ichiro Nishimura. Chem. Commun. 1944-1945, 2001) were treated with restriction enzymes of NdeI and BamHI to construct an expression vector of MBP-GalT in which a membrane-binding peptide was fused to a C terminal. The vector was transformed to *E. coli* JM109 strain to prepare *E. coli* variant. After the product was cultured on 4 mL of 2×YT medium at 37° C. overnight, the culture solution was subcultured on 200 mL of 2×YT medium and cultured at 37° C. for 2 hours. IPTG was added to the culture solution so that a final concentration thereof reached 1 mM and cultured at 20° C. for 20 hours.

The culture solution was subjected to centrifugal separation at 10,000×g for 20 minutes to collect bacterial cells and suspended in 5 mL of 25 mM Tris buffer solution (pH8.0) containing 1 mM mercaptoethanol and 10% (w/v) glycerol, and ultrasonic crushing of bacterial cells was performed 5 times for 2 minutes each under cooling by ultrasonic crusher. After another centrifugal separation at 10,000×g for 20 minutes, supernatants were collected to be purified by anion-exchange column (DEAE FF; Amersham Pharmacia Biotech). Subsequently, after adsorbed fractions were subjected to Ni column (His Trap FF; Amersham Pharmacia Biotech)

under alkaline conditions (pH 8 to 10), they were condensed by ultrafiltration under alkaline conditions (pH 8 to 10) to obtain purified membrane-binding peptide-fused MBP-GalT (1.6 mg/mL).

(2) Preparation of MBP-GalT-Immobilized Magnetic Microparticle

By presenting a membrane-binding peptide-fused MBP-Gal obtained in this Example 9(1) to a biomembrane mimetic magnetic microparticle, MBP-GalT-immobilized magnetic microparticle was prepared. Specifically, 100 4 of membrane-binding peptide-fused MBP-Gal solution (160 μg) obtained in this Example 9(1) was added to biomembrane-mimicking magnetic microparticle prepared by a method as in Example 1(2) and agitated at 4° C. for 2 hours. Thereafter, all of the solutions were removed and the biomembrane mimetic magnetic microparticle was washed with 100 4, of 100 mM Tris buffer solution (pH7.5) 5 times. The step can present an MBP-GalT having membrane-binding peptide on a C terminal to a biomembrane mimetic magnetic microparticle, and MBP-GalT-immobilized magnetic microparticle in which MBP-GalT was immobilized to magnetic microparticle via a membrane-binding peptide and an organic membrane (biomimetic membrane) was obtained.

(3) Measurement of Activity of MBP-GalT-Immobilized Magnetic Microparticle

Subsequently, MBP-GalT activity for 4MU-GlcNAc of MBP-GalT-immobilized magnetic microparticle obtained in this Example 9(2) was measured and whether MBP-GalT which was immobilized to a magnetic microparticle via a membrane-binding peptide and an organic membrane (biomimetic membrane) has an activity or not was confirmed. Specifically, 50 μL of substrate solution prepared by a method as in Example 4(4) was added to MBP-GalT-immobilized magnetic microparticle prepared in this Example 9(2) and reacted at room temperature for 2 hours. Thereafter, 1 μL of 10 mg/mL DHB was mixed with 1 μL of the reaction liquid to measure an activity thereof by MALDI-TOF-MS by a method as in Example 1(3) [3-2]. As a control, an activity of free membrane-binding peptide-fused MBP-GalT which was not immobilized to a magnetic microparticle was also measured. Measurement results of free membrane-binding peptide-fused MBP-GalT are shown in FIG. 27(a), and measurement results of MBP-GalT-immobilized magnetic microparticle are shown in FIG. 27(b).

Figure 27:
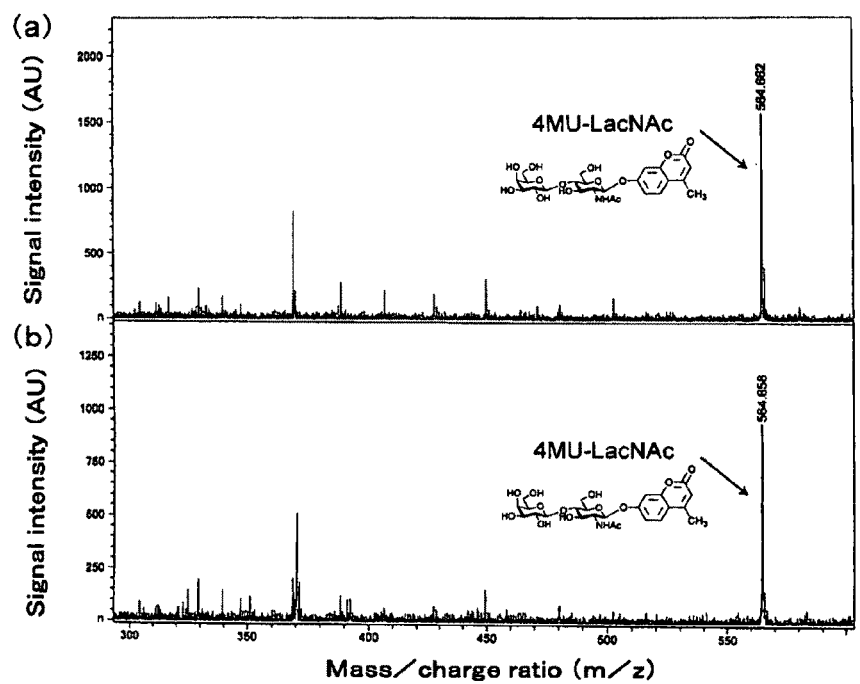
FIG. 27 is a spectral chart by the measurement of 4MU-LacNAc after reaction, using MALDI-TOF-MS to measure activity of free membrane-binding peptide-fused MBP-GalT and MBP-GalT-immobilized magnetic microparticle of Example 9(3) ((a) and (b) are spectral charts for free membrane-binding peptide-fused MBP-GalT and MBP-GalT-immobilized magnetic microparticle, respectively).

As shown in FIGS. 27(a) and (b), in both free membrane-binding peptide-fused MBP-GalT and MBP-GalT-immobilized magnetic microparticle, only a peak corresponding to a compound in which galactose was transferred (peaks of 564.662 and 564.658 in 4MU-LacNAc) was detected. Specifically, as in case of free membrane-binding peptide-fused MBP-GalT, an activity of MBP-GalT-immobilized magnetic microparticle was confirmed.

The above observation found that a membrane-binding peptide-fused MBP-GalT can be immobilized to a biomembrane mimetic magnetic microparticle, with activity maintained, and the product can be used as MBP-GalT-immobilized magnetic microparticle.

Example 10

Preparation of N-Acetylgalactosamine Transferase 2 (ppGalNAcT2) Immobilized Magnetic Microparticle In Vivo and Measurement of Enzyme Activity Using N-acetylgalactosamine transferase 2 (ppGalNAcT2) which is an enzyme transferring N-acetylgalactosamine to threonine or serine side-chain hydroxyl group as a biomolecule, a membrane-binding peptide-fused ppGalNAcT2 incorporating a polypeptide of 42 residues containing membrane-binding peptide in a C terminal of the ppGalNAcT2 was prepared in vivo, and by presenting the membrane-binding peptide-fused ppGalNAcT2 to biomembrane-mimicking magnetic microparticle, ppGalNAcT2-immobilized magnetic microparticle was prepared and an activity thereof was measured.

(1) Preparation of Membrane-Binding Peptide-Fused ppGalNacT2 In Vivo ppGalNAcT2 was cloned from cDNA derived from small intestines (Invitrogen) to obtain a vector in which ppGalNAcT2 was constructed (Tabak, L A et al. JBC. 2006, 281, 8613-8619). The vector and fragments encoding a polypeptide of 42 residues containing a membrane-binding peptide prepared in Example 8 were treated with restriction enzymes of NdeI and BamHI to construct an expression vector of ppGalNAcT2 in which membrane-binding peptide was fused to a C terminal. The vector was transformed to methanol utilizing yeast to prepare yeast variant. After the product was cultured in 50 mL of YPAD medium at 37° C. overnight, the culture solution was subcultured in 500 mL of YPAD medium, and by adding 2.5 mL of methanol thereto every 24 hours, the product was further cultured at 20° C. for total 72 hours.

The culture solution was subjected to centrifugal separation at 10,000×g for 20 minutes to remove bacterial cells, and supernatants containing membrane-binding peptide-fused ppGalNAcT2 were collected and subjected to Ni column (His Trap FF; Amersham Pharmacia Biotech) under alkaline conditions (pH 8 to 10). Thereafter, the product was condensed by ultrafiltration under alkaline conditions (pH 8 to 10) to obtain purified membrane-binding peptide-fused ppGalNAcT2v (1.5 mg/mL).

(2) Preparation of ppGalNAcT2-Immobilized Magnetic Microparticle

By presenting a membrane-binding peptide-fused ppGalNAcT2 obtained in this Example 10(1) to a biomembrane mimetic magnetic microparticle, ppGalNAcT2-immobilized magnetic microparticle was prepared. Specifically, 40 μL of membrane-binding peptide-fused ppGalNAcT2 solution (60 μg) obtained in this Example 10(1) was added to a biomembrane-mimicking magnetic microparticle prepared in a method as in Example 1(2) and agitated at 4° C. for 2 hours. Thereafter, all of the solutions were removed and the biomembrane mimetic magnetic microparticle was washed with 100 μL of 50 mM Tris-HCL buffer solution (pH7.5) 7 times. This step can present ppGalNAcT2 having membrane-binding peptide on a C terminal to magnetic microparticle, and ppGalNAcT2-immobilized magnetic microparticle in which ppGalNAcT2 was immobilized to a magnetic microparticle via a membrane-binding peptide and an organic membrane (biomimetic membrane) was obtained.

(3) Preparation of ppGalNAcT2 Nonspecific Adsorption Magnetic Microparticle

As a control, by mixing 40 μL (60 μg) of ppGalNAcT2 with Ag-coated magnetic microparticle using the above-mentioned step, ppGalNAcT2 nonspecific adsorption magnetic microparticle, in which ppGalNAcT2 was nonspecifically adsorbed, was prepared.

(4) Measurement of Activity of ppGalNAcT2-Immobilized Magnetic Microparticle and ppGalNAcT2 Nonspecific Adsorption Magnetic Microparticle Subsequently, ppGalNAcT2 activity for MUC5AC mucin of ppGalNAcT2-immobilized magnetic microparticle obtained in this Example 10(2) and ppGalNAcT2 nonspecific adsorption magnetic microparticle obtained in this Example 10(3) was measured. Specifically, 5 µL of 100 mM manganese chloride, 10 µL of 10 mM uridine 5'-2phosphoric acid-α-D-N-acetylgalactosamine, 1.25 µL of 10 mM MUC5AC mucin peptide (GTTPSPVPTTSTTSA-NF12) (SEQ ID NO: 7) and 2.5 µL of 1M Tris-HCL buffer solution (pH7.5) were mixed with 36.25 µL of ultrapure water to prepare a substrate solution. The substrate solution was added to 1 mg of ppGalNAcT2-immobilized magnetic microparticle and 1 mg of ppGalNAcT2 nonspecific adsorption magnetic microparticle prepared in this Examples 10(2) and (3), respectively, each by 50 µL, and reacted at 37° C. for one hour. 1 µL of 10 mg/mL DHB was mixed with 14 of reaction liquid to measure an activity thereof by MALDI-TOF-MS by a method as in Example 1(3) [3-2]. Measurement results of ppGalNAcT2-immobilized magnetic microparticle are shown in FIG. 28(a), and measurement results of ppGalNAcT2 nonspecific adsorption magnetic microparticle as a control are shown in FIG. 28(b).

Figure 28:
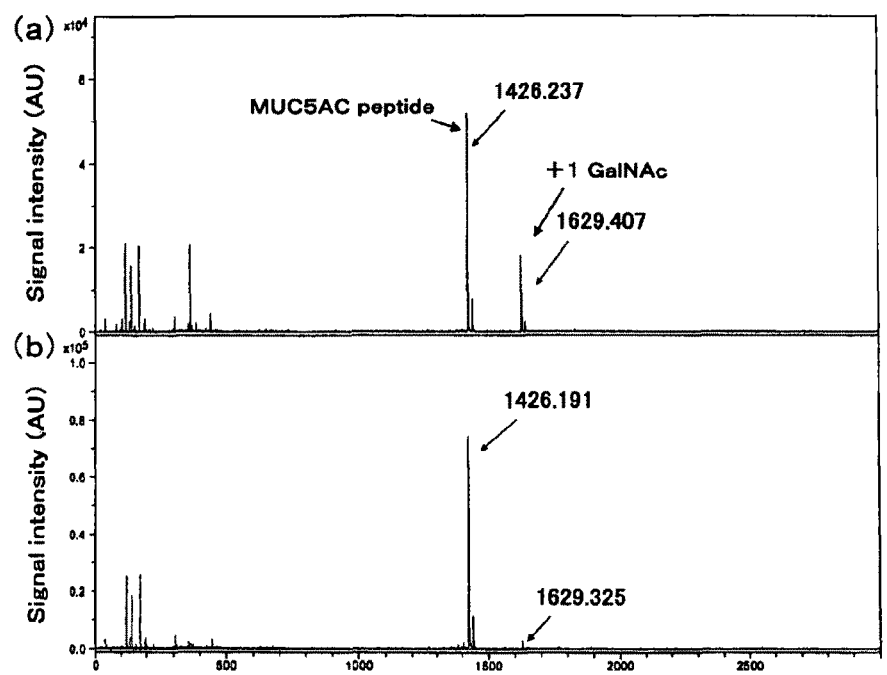
FIG. 28 is a spectral chart by the measurement of a compound in which an N-acetylgalactosamine after reaction is transferred, using MALDI-TOF-MS to measure activity of ppGalNAcT2-immobilized magnetic microparticle and ppGalNAcT2 nonspecific adsorption magnetic microparticle of Example 10(4) ((a) and (b) are spectral charts for ppGalNAcT2-immobilized magnetic microparticle and ppGalNAcT2 nonspecific adsorption magnetic microparticle, respectively).

As shown in FIG. 28(b), a peak corresponding to a compound, in which (peak of 1629.325) one N-acetylgalactosamine was transferred, was scarcely detected in ppGalNAcT2 nonspecific adsorption magnetic microparticle, and enzyme activity of ppGalNAcT2 was hardly confirmed. Meanwhile, as shown in FIG. 28(a), a peak corresponding to a compound, in which one N-acetylgalactosamine was transferred (peak of 1629.407), was detected in ppGalNAcT2-immobilized magnetic microparticle, and enzyme activity of ppGalNAcT2 was confirmed.

The above observation found that a membrane-binding peptide-fused ppGalNAcT2 can be immobilized to a biomembrane mimetic magnetic microparticle, with activity maintained, and the product can be used as ppGalNAcT2-immobilized magnetic microparticle.

The above-mentioned Examples can provide a biomolecule-immobilized carrier capable of controlling molecular orientation with biomolecule activity maintained due to excellent durability and being readily handled due to solubilization of a membrane-binding molecule, particularly a biomolecule-immobilized magnetic microparticle and a probe-immobilized carrier using a biomolecule having said membrane-binding peptide and/or said membrane-binding molecule as a probe. For example, in case of a biomolecule-immobilized microarray using sugar chain as a biomolecule, a protein (marker) which recognizes and binds sugar chain as a probe can be fished. When sugar chain which is specifically expressed in cancer, etc is immobilized via a membrane-binding peptide and an organic membrane (biomimetic membrane), this invention can be used as a diagnostic tool for identifying cancer only by flowing patient's serum.

A biomolecule-immobilized carrier and a method for immobilizing a biomolecule to a carrier according to the present invention are not limited to the above Examples, but may be altered accordingly.

SUMMARY OF SEQUENCES

Sequence Listing

<110> National University Corporation Hokkaido University
<120> BIOMOLECULE-IMMOBILIZED CARRIER AND METHOD FOR IMMOBILIZING BIOMOLECULE ON CARRIER
<130> 374698-000001
<140> U.S. Ser. No. 12/735,837
<141> 2010-11-29
<150> PCT/JP2009/053038
<151> 2009-02-20
<160> 11
<170> PatentIn version 3.5

The invention claimed is:

1. A carrier-immobilized biomolecule comprising:
   (a) a membrane-binding molecule comprising (i) a membrane-binding peptide linked to or bound to (ii) a biomolecule, immobilized on
   (b) a carrier coated with a phospholipid-comprising layer, wherein the phospholipid in the phospholipid-comprising layer comprises: (i) in a first region of the phospholipid a fixed ligand that binds to or adsorbs to the carrier, whereby the carrier is coated with the layer of the phospholipid and (ii) a second region that binds to the membrane-binding peptide, thereby linking the membrane-binding molecule to the carrier,
      wherein the membrane-binding peptide comprises the polypeptide of SEQ ID NO: 1 or SEQ ID NO: 8, or SEQ ID NO: 9,
      wherein the biomolecule is selected from the group consisting of: DNA, RNA, peptide nucleic acid (PNA), aptamer, chromosome, peptide, enzyme, monosaccharide, oligosaccharide, polysaccharide, sugar chain complex, glycoprotein, glycolipid, glycolipid, glyceride, antibody, antigen, and hapten; and wherein the carrier is selected from the group consisting of: a magnetic microparticle, an organic polymer metal oxide, metal, semiconductor compound, agarose, wooden plate, glass plate, silicon substrate, cotton cloth, rayon cloth, silk cloth, wood-free paper, wood-containing paper, art paper, bond paper, recycled paper, baryta paper, cast-coated paper, corrugated paper and resin-coated paper.

2. The carrier-immobilized biomolecule as set forth in claim 1, wherein said carrier is a magnetic microparticle.

3. The carrier-immobilized biomolecule as set forth in claim 2, wherein said biomolecule is an enzyme, a sugar chain complex, or a glycoprotein.

4. The carrier-immobilized biomolecule as set forth in claim 3, wherein said enzyme is glycosyl transferase or glycosidase.

5. The carrier-immobilized biomolecule as set forth in claim 1, wherein said biomolecule is an enzyme, a sugar chain complex, or a glycoprotein.

6. The carrier-immobilized biomolecule as set forth in claim 5, wherein said enzyme is glycosyl transferase or glycosidase.

7. The carrier-immobilized biomolecule as set forth in claim 1, wherein the membrane-binding molecule is released from the carrier coated with the phospholipid-comprising layer under alkaline conditions, and the membrane-binding molecule is immobilized to the carrier coated with the phospholipid comprising layer under neutral conditions.

8. The carrier-immobilized biomolecule as set forth in claim 1, wherein said biomolecule is a glycoprotein.

9. An agent for separating a biomolecule comprising:
a membrane-binding peptide and/or a membrane-binding molecule comprising said membrane-binding peptide, immobilized to a magnetic microparticle coated with a phospholipid-comprising layer, wherein the membrane-binding peptide comprises the polypeptide of SEQ ID NO: 1.

10. A method for immobilizing a biomolecule to a carrier, comprising:
(a) providing a phospholipid having:

(i) a fixed ligand in a first region of the phospholipid, wherein the fixed ligand is configured for adsorbing or linking the phospholipid to the carrier and (ii) a second region of the phospholipid, wherein the second region is capable of binding the phospholipid to a membrane-binding peptide;

(b) adsorbing or directly linking the phospholipid-fixed ligand to the carrier, in an amount thereof sufficient to form a carrier coated with a layer of the phospholipid;
(c) providing a membrane-binding molecule comprising:

(i) a membrane-binding peptide, wherein the peptide comprises the polypeptide of SEQ ID NO: 1, SEQ ID NO: 8, or SEQ ID NO: 9, wherein said peptide is linked to or bound to (ii) a biomolecule, selected from the group consisting of a(n): DNA, RNA, peptide nucleic acid (PNA), aptamer, chromosome, peptide, enzyme, monosaccharide, oligosaccharide, polysaccharide, sugar chain complex, glycoprotein, glycolipid, glycolipid, glyceride, antibody, antigen, and hapten; and (d) contacting the phospholipid-coated carrier second region with the membrane-binding peptide of the membrane-binding molecule, thereby forming a carrier-immobilized biomolecule; wherein the carrier is selected from the group consisting of a(n): magnetic microparticle, organic polymer metal oxide, metal, semiconductor compound, agarose, wooden plate, glass plate, silicon substrate, cotton cloth, rayon cloth, silk cloth, wood-free paper, wood-containing paper, art paper, bond paper, recycled paper, baryta paper, cast-coated paper, corrugated paper and resin-coated paper.

11. The method of claim 10, wherein the providing of the membrane-binding molecule having the membrane-binding peptide linked to or bound to the biomolecule of step (c) further comprises linking or binding the membrane-binding peptide to the biomolecule.

* * * * *

SEQUENCE LISTING

<160> NUMBER OF SEQ ID NOS: 11

<210> SEQ ID NO 1
<211> LENGTH: 23
<212> TYPE: PRT
<213> ORGANISM: Artificial Sequence
<220> FEATURE:
<223> OTHER INFORMATION: membrane binding peptide

<400> SEQUENCE: 1

Lys Ile Tyr Arg Lys Ala Tyr Gln Lys Ser Leu Pro Leu Leu Arg Thr
1               5                   10                  15

Ile Arg Arg Trp Val Lys Lys
            20

<210> SEQ ID NO 2
<211> LENGTH: 69
<212> TYPE: DNA
<213> ORGANISM: Artificial Sequence
<220> FEATURE:
<223> OTHER INFORMATION: codes for membrane binding protein

<400> SEQUENCE: 2
aaaatctatc gcaaagccta tcaaaaatcc ttacctttgt tgcgcaccat aaggagatgg      60
gttaaaaaa                                                             69

<210> SEQ ID NO 3

```
<211> LENGTH: 29
<212> TYPE: DNA
<213> ORGANISM: Artificial Sequence
<220> FEATURE:
<223> OTHER INFORMATION: sense primer

<400> SEQUENCE: 3
caaagcttga tcgcctttta caaaacgct                                    29

<210> SEQ ID NO 4
<211> LENGTH: 27
<212> TYPE: DNA
<213> ORGANISM: Artificial Sequence
<220> FEATURE:
<223> OTHER INFORMATION: antisense primer

<400> SEQUENCE: 4
ctgtgactgg tgagtactca accaagt                                      27

<210> SEQ ID NO 5
<211> LENGTH: 7
<212> TYPE: PRT
<213> ORGANISM: Artificial Sequence
<220> FEATURE:
<223> OTHER INFORMATION: chemically synthesized peptide

<400> SEQUENCE: 5

Asp Asp Leu Arg Val Asn Tyr
1               5

<210> SEQ ID NO 6
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 6

Leu Pro Glu Thr Gly
1               5

<210> SEQ ID NO 7
<211> LENGTH: 15
<212> TYPE: PRT
<213> ORGANISM: Artificial Sequence
<220> FEATURE:
<223> OTHER INFORMATION: chemically synthesized peptide

<400> SEQUENCE: 7

Gly Thr Thr Pro Ser Pro Val Pro Thr Thr Ser Thr Thr Ser Ala
1               5                   10                  15

<210> SEQ ID NO 8
<211> LENGTH: 42
<212> TYPE: PRT
<213> ORGANISM: Artificial Sequence
<220> FEATURE:
<223> OTHER INFORMATION: chemically synthesized peptide

<400> SEQUENCE: 8

Asp Arg Leu Leu Gln Asn Ala Ser Pro Leu Leu Glu Leu Ser Gln Asn
1               5                   10                  15

Thr Thr Phe Lys Ile Tyr Arg Lys Ala Tyr Gln Lys Ser Leu Pro Leu
            20                  25                  30

Leu Arg Thr Ile Arg Arg Trp Val Lys Lys
            35                  40
```

```
<210> SEQ ID NO 9
<211> LENGTH: 47
<212> TYPE: PRT
<213> ORGANISM: Artificial Sequence
<220> FEATURE:
<223> OTHER INFORMATION: chemically synthesized peptide

<400> SEQUENCE: 9

Leu Pro Glu Thr Gly Asp Arg Leu Leu Gln Asn Ala Ser Pro Leu Leu
1               5                   10                  15

Glu Leu Ser Gln Asn Thr Thr Phe Lys Ile Tyr Arg Lys Ala Tyr Gln
            20                  25                  30

Lys Ser Leu Pro Leu Leu Arg Thr Ile Arg Arg Trp Val Lys Lys
        35                  40                  45

<210> SEQ ID NO 10
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 10

Leu Pro Lys Thr Gly
1               5

<210> SEQ ID NO 11
<211> LENGTH: 17
<212> TYPE: PRT
<213> ORGANISM: Artificial Sequence
<220> FEATURE:
<223> OTHER INFORMATION: chemically synthesized peptide

<400> SEQUENCE: 11

Val Thr Ser Ala Pro Asp Thr Arg Pro Ala Leu Pro Lys Thr Gly Leu
1               5                   10                  15

Arg
```